(12) United States Patent
Froguel et al.

(10) Patent No.: US 8,017,324 B1
(45) Date of Patent: Sep. 13, 2011

(54) ENPP1 (PC-1) GENE HAPLOTYPE ASSOCIATED WITH THE RISK OF OBESITY AND TYPE 2 DIABETES AND THEIR APPLICATIONS

(75) Inventors: Philippe Froguel, Bagnolet (FR); David Meyre, Marpent (FR); Christian Dina, Paris (FR); Philippe Boutin, Tourcoing (FR)

(73) Assignees: Centre National de la Recherche Scientifique, Paris (FR); Universite de Droit de la La Sante de Lille 2, Lille (FR)

( * ) Notice: Subject to any disclaimer, the term of this patent is extended or adjusted under 35 U.S.C. 154(b) by 515 days.

(21) Appl. No.: 11/917,586

(22) PCT Filed: Jun. 15, 2006

(86) PCT No.: PCT/EP2006/063256
§ 371 (c)(1),
(2), (4) Date: Mar. 6, 2008

(87) PCT Pub. No.: WO2006/134154
PCT Pub. Date: Dec. 21, 2006

(30) Foreign Application Priority Data

Jun. 17, 2005  (EP) .................................. 05291298

(51) Int. Cl.
*C12Q 1/68* (2006.01)
*C12P 19/34* (2006.01)
*C07H 21/02* (2006.01)
*C07H 21/04* (2006.01)
*G01N 33/53* (2006.01)

(52) U.S. Cl. ................ 435/6; 435/4; 435/7.1; 435/91.1; 435/91.2; 536/23.5; 536/24.31; 536/24.33

(58) Field of Classification Search .................. None
See application file for complete search history.

(56) References Cited

U.S. PATENT DOCUMENTS
6,465,185 B1   10/2002   Goldfine et al.

OTHER PUBLICATIONS

Hirschhorn et al. Genetics in Medicine. vol. 4, No. 2, pp. 45-61, Mar. 2002.*
Lucentini et al. The Scientist. 2004 vol. 18, p. 20.*
Wacholder et al. J. Natl. Cancer Institute. 2004. 96(6):434-442.*
Halushka. Nature. Jul. 1999. 22: 239-247.*
Morandi et al. Obesity. 2009. 17: 202-206.*
Lyon et al. Diabetes. 2006. 55: 3180-3184.*
Weedon et al. Diabetes. 2006. 55: 3175-3179.*
Abate et al., "Genetic Polymorphism PC-1 K121Q and Ethnic Susceptibility to Insulin Resistance," J. Clin. Endocrinol. Metab., 2003, pp. 5927-5934, vol. 88(12).
Abney, et al., "Quantitative-Trait Homozygosity and Association Mapping and Empirical Genomewide Significance in Large, Complex Pedigrees: Fasting Serum-Insulin Level in Hutterites" Am. J. Hum. Genet., 2002, pp. 920-934, vol. 70.
Atwood, et al., "Genomewide Linkage Analysis of Body Mass Index Across 28 Years of the Framingham Heart, Study," Am. J. Hum. Genet., 2002, pp. 1044-1050, vol. 71.
Barroso et al., "Candidate Gene Association Study in Type 2 Diabetes Indicates a Role for Genes Involved in Beta-Cell Function as Well as Insulin Action," PLoS Biol., 2003, pp. 014-055, vol. 1(1).
Bruning et al., "Role of Brain Insulin Receptor in Control of Body Weight and Reproduction," Science, 2000, pp. 2122-2125, vol. 289.
Cole, "The LMS Method for Constructing Normalized Growth Standards," Eur. J. Clin. Nutr., 1990, pp. 45-60, vol. 44.
Costanzo et al., "The Q Allele Variant (GLN$^{121}$) of Membrane Glycoprotein PC-1 Interacts With the Insulin Receptor and Inhibits Insulin Signaling More Effectively Than the Common K Allele Variant (LYS$^{121}$)," Diabetes, 2001, pp. 831-836, vol. 50.
Demenais et al., "A Meta-Analysis of Four European Genome Screens (GIFT Consortium) Shows Evidence for a Novel Region on Chromosome 17p11.2-q22 linked to Type 2 Diabetes," Hum. Mol. Genet., 2003, pp. 1865-1873, vol. 12(15).
Deng et al., "QTL Fine Mapping by Measuring and Testing for Hardy-Weinberg and Linkage Disequilibrium at a Series of Linker Marker Loci in Extreme Samples of Populations," Am. J. Hum. Genet., 2000, pp. 1027-1045, vol. 66.
Dong et al., "Increased Hepatic Levels of the Insulin Receptor Inhibitor, PC-1/NPP1, Induce Insulin Resistance and Glucose Intolerance," Diabetes, 2005, pp. 367-372, vol. 54.
Dudbridge et al., "Unbiased Application of the Transmission/Disequilibrium Test to Multilocus Haplotypes," Am. J. Hum. Genet., 2000, pp. 2009-2012, vol. 66.
Duggirala et al., "A Major Locus for Fasting Insulin Concentrations and Insulin Resistance on Chromosome 6q With Strong Pleiotropic Effects on Obesity-Related Phenotypes in Nondiabetic Mexican Americans," Am. J. Hum. Genet., 2001, pp. 1149-1164, vol. 1168.
Eaves et al., "Transmission Ratio Distortion at the INS-IGF2 VNTR," Nat. Genet., 1999, pp. 324-325, vol. 22. Frittitta et al., "A Cluster of Three Single Nucleotide Polymorphisms in the 3'-Untranslated Region of Human Glycoprotein PC-1 Gene Stabilizes PC-1 mRNA and is Associates With Increased PC-1 Protein Content and Insulin Resistance-Related Abnormalities," Diabetes, 2001, pp. 1952-1955, vol. 50(8).
Frittitta et al., "The Q121 PC-1 Variant and Obesity Have Additive and Independent Effects in Causing Insulin Resistance," Journal of Clinical Endocrinology and Metabolism, 2001, pp. 5888-5891, vol. 86(12).
Gelder, et al., "Genomewide Search for Type 2 Diabetes Susceptibility Genes in Four American Populations," Am. J. Hum. Genet., 2000, pp. 1871-1881, vol. 66.
Ghosh et al., "The Finland-United States Investigation of Non-Insulin-Dependent Diabetes Mellitus Genetics (FUSION) Study. I. An Autosomal Genome Scan for Genes That Predispose to Type 2 Diabetes," Am. J. Hum. Genet., 2000, pp. 1174-1185, vol. 67.

(Continued)

*Primary Examiner* — Carla Myers
(74) *Attorney, Agent, or Firm* — Alston & Bird LLP

(57) ABSTRACT

The present invention is directed to a method for determining if a subject is at increased risk to develop obesity or pathology related to obesity by determining the presence of a haplotype comprising three specific SNPs in a DNA or RNA sample of this subject and/or an elevated serum ENPP1 protein concentration. The present invention also relates to a kit and to an isolated nucleic sequence, vector or recombinant cell comprises said ENPP1 gene haplotype. The invention further comprises a method for selecting a compound for the treatment or the prevention of obesity or pathology related to obesity and a method for determining the efficacy of a drug to reduce the risk of obesity or pathology related to obesity in a patient.

9 Claims, 5 Drawing Sheets

OTHER PUBLICATIONS

Figure 1:
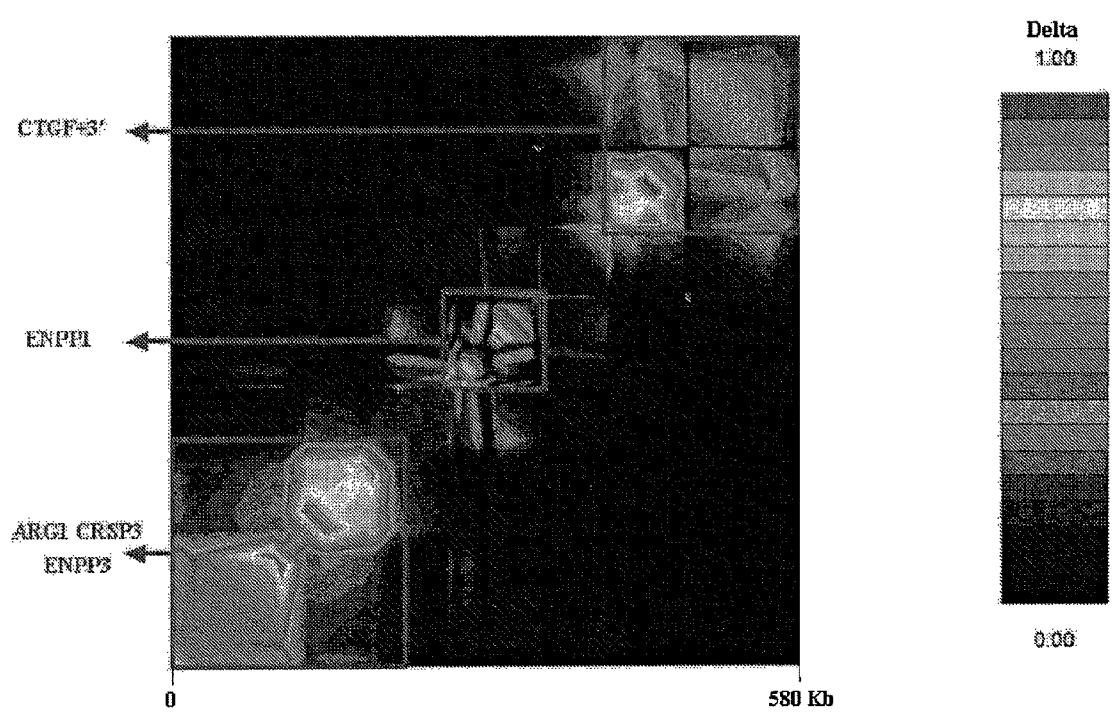

Goding et al., "Physiological and Pathophysiological Functions of the Ecto-Nucleotide Pyrophosphatase/Phosphodiesterase Family," Biochimica Et Biophysica Acta. Molecular Basis of Disease, Amsterdam, NL, May 20, 2003, pp. 1-19, vol. 1638(1).

Gu et al., "Association Between the Human Glycoprotein PC-1 Gene and Elevated Glucose and Insulin Levels in a Paired-Sibling Analysis," Diabetes, 2000, pp. 1601-1603, vol. 49.

Hager et al., "A Genome-Wide Scan for Human Obesity Genes Reveals a Major Susceptibility Locus on Chromosome 10," Nat. Genet., 1998, pp. 304-308, vol. 20.

Hamaguchi et al., "The PC-1 Q121 Allele is Exceptionally Prevalent in the Dominican Republic and is Associated With Type 2 Diabetes," Journal of Clinical Endocrinology & Metabolism, 2004, pp. 1359-1364, vol. 89(3).

Hampe et al., "Evidence for a NOD2-Independent Susceptibility Locus for Inflammatory Bowel Disease on Chromosome 16p" Proc. Natl. Acad. Sci. USA, 2002, pp. 321-326, vol. 99.

Hercberg et al., "A Primary Prevention Trial Using Nutritional Doses of Antioxidant Vitamins and Minerals in Cardiovascular Diseases and Cancers in a General Population: the SU.VI.MAX Study-Design, Methods, and Participant Characteristics. Supplementation en Vitamines et Mineraux AntioXydants," Control Clin. Trials, 1998, pp. 336-351, vol. 19.

Holder et al., "Profound Obesity Associated With a Balanced Translocation That Disrupts the SIMI Gene," Hum. Mol. Genet., 2000, pp. 101-108, vol. 9.

Hugot et al., "Association of NOD2 Leucine-Rich Repeat Variants With Susceptibility to Crohn's Disease," Nature, 2001, pp. 599-603, vol. 411.

Jenkinson et al., "Comprehensive analysis of snps in ENPP1: Association With Diabesity," ASHG, 2004, abstract.

Johnson et al., "Longitudinal Changes in Body Fat in African American and Caucasian Children: Influence of Fasting Insulin and Insulin Sensitivity," J. Clin. Endocrinol. Metab., 2001, pp. 3182-3187, vol. 86(7).

Kim et al., "Redistribution of Substrates to Adipose Tissue Promotes Obesity in Mice With Selective Insulin Resistance in Muscle," J. Clin. Invest., 2000, pp. 1791-1797, vol. 105(12).

Kruglyak et al., "Complete Multipoint Sib-Pair Analysis of Qualitative and Quantitative Traits," Am. J. Hum. Genet., 1995, pp. 439-454, vol. 57.

Kubaszek, et al., "The K121Q Polymorphism of the PC-1 Gene is Associated With Insulin Resistance But Not With Dyslipidemia," Diabetes Care, 2003, pp. 464-467, vol. 26.

Kulkarni et al., "Tissue-Specific Knockout of the Insulin Receptor in Pancreatic Beta Cells Creates an Insulin Secretory Defect Similar to That in Type 2 Diabetes," Cell, 1999, pp. 329-339, vol. 96.

Lafay et al., "Determinants and Nature of Dietary Underreporting in a Free-Living Population: the Fleurbaix Laventie Ville Sante (FLVS) Study," Int. J. Obes. Relat. Metab. Disord., 1997, pp. 567-573, vol. 21.

Li et al., "Assessing whether an Allele Can Account in Part for a Linkage Signal: the Genotype-IBD Sharing Test (GIST)," Am. J. Hum. Genet., 2004, pp. 418-431, vol. 74.

Lukowiak et al., "Identification and Purification of Functional Human Beta-Cells by a New Specific Zinc-Fluorescent Probe," J. Histochem. Cytochem., 2001, pp. 519-528, vol. 49(4).

Maddux et al., "Membrane Glycoprotein PC-1 and Insulin Resistance in Non-Insulin-Dependent Diabetes Mellitus," Nature, 1995, pp. 448-451, vol. 373.

Maddux et al., "Membrane Glycoprotein PC-1 Inhibition of Insulin Receptor Function Occurs Via Direct Interaction With the Receptor Alpha-Subunit," Diabetes, 2000, pp. 13-19, vol. 49.

Meyre et al., "A Genome-Wide Scan for Childhood Obesity-Associated Traits in French Families Shows Significant Linkage on Chromosome 6q22.31-q23.2," Diabetes, 2004, pp. 803-811, vol. 53.

Meyre et al., "Variants of ENPP1 Are Associates With Childhood and Adult Obesity and Increase the Risk of Glucose Intolerance and Type 2 Diabetes," Nature Genetics, Aug. 2005, pp. 863-867, vol. 37(8).

Michael et al., "Loss of Insulin Signaling in Hepatocytes Leads to Severe Insulin Resistance and Progressive Hepatic Dysfunction," Mol. Cell, 2000, pp. 87-97, vol. 6.

Michaud et al., "Sim1 Haploinsufficiency Causes Hyperphagia, Obesity and Reduction of the Paraventricular Nucleus of the Hypothalamus," Hum. Mol. Genet., 2001, pp. 1465-1473, vol. 10(14).

Oberkofler et al., "Complex Haplotypes of the PGC-1alpha Gene are Associated With Carbohydrate Metabolism and Type 2 Diabetes," Diabetes, 2004, pp. 1385-1393, vol. 53.

Odeleye et al., "Fasting Hyperinsulinemia is a Predictor of Increased Body Weight Gain and Obesity in Pima Indian Children," Diabetes, 1997, pp. 1341-1345, vol. 46.

Ohlsson et al., "IPF1 a Homeodomain-Containing Transactivator of the Insulin Gene," Embo J., 1993, pp. 4251-4259, vol. 12.

Pizzuti et al., "A Polymorphism (K121Q) of the Human Glycoprotein PC-1 Gene Coding Region is Strongly Associated With Insulin Resistance," Diabetes, 1999, pp. 1881-1884, vol. 48.

Poskitt, "Defining Childhood Obesity: the Relative Body Mass Index (BMI), European Childhood Obesity Group," Acta Paediatr, 1995, pp. 961-963, vol. 84.

Risch, "Linkage Strategies for Genetically Complex Traits. I. Multilocus Models," Am. J. Hum. Genet., 1990, pp. 222-228, vol. 46.

Rolland-Cachera, et al., "Body Mass Index Variations: Centiles From Birth to 87 Years," Eur. J. Clin. Nutr., 1991, pp. 13-21, vol. 45.

Rutsch et al., "PC-1 Nucleoside Triphosphate Pyrophosphohydrolase Deficiency in Idiopathic Infantile Arterial Calcification," Am. J. Pathol., 2001, pp. 543-554, vol. 158.

Schwartz, "Progress in the Search for Neuronal Mechanisms Coupling Type 2 Diabetes to Obesity," J. Clin. Invest., 2001, pp. 963-964, vol. 108(7).

Seltzer et al., "Insulin Secretion in Response to Glycemic Stimulus: Relation of Delayed Initial Release to Carbohydrate Intolerance in Mild Diabetes Mellitus," J. Clin. Invest., 1967, pp. 323-335, vol. 46(3).

Sham et al., "Monte Carlo Tests for Associations Between Disease and Alleles at High Polymorphic Loci," Am. J. Hum. Genet., 1995, pp. 97-105, vol. 59.

Stefanovic et al., "Plasma Cell Membrane Glycoprotein 1 (PC-1): A Marker of Insulin Resistance in Obesity, Uremia and Diabetes Mellitus," Clinical Laboratory, 2004, pp. 271-278, vol. 50(5-6).

Tregouet et al., "A New Algorithm for Haplotype-based Association Analysis: the Stochastic-EM Algorithm," Ann. Hum. Genet., 2004, pp. 165-177, vol. 68.

Um et al., "Absence of S6K1 Protects Against Age- and Diet-Induced Obesity While Enhancing Insulin Sensitivity," Nature, 2004, pp. 200-205, vol. 431.

Weill et al., "Understanding the Rising Incidence of Type 2 Diabetes in Adolescence," Arch. Dis. Child, 2004, pp. 502-504, vol. 89.

Xiang et al., "Genome-Wide Search for Type 2 Diabetes/Impaired Glucose Hemostatis Susceptibility Genes in the Chinese: Significant Linkage to Chromosome 6q21-q23 and Chromosome 1q21-q24," Diabetes, 2004, pp. 228-234, vol. 53.

International Search Report of International App. No. PCT/EP2006/063256, dated Nov. 24, 2006.

\* cited by examiner

ENPP1 (PC-1) GENE HAPLOTYPE ASSOCIATED WITH THE RISK OF OBESITY AND TYPE 2 DIABETES AND THEIR APPLICATIONS

The present invention is directed to a method for determining if a subject is at increased risk to develop obesity or pathology related to obesity by determining the presence of a haplotype comprising three specific SNPs in a DNA or RNA sample of this subject and/or an elevated serum ENPP1 protein concentration. The present invention also relates to a kit and to an isolated nucleic sequence, vector or recombinant cell comprises said ENPP1 gene haplotype. The invention further comprises a method for selecting a compound for the treatment or the prevention of obesity or pathology related to obesity and a method for determining the efficacy of a drug to reduce the risk of obesity or pathology related to obesity in a patient.

Obesity is a devastating disease. In addition to harming physical health, obesity can wreak havoc on mental health because obesity affects self-esteem, which ultimately can affect a person's ability to interact socially with others. Unfortunately, obesity is not well understood, and societal stereotypes and presumptions regarding obesity only tend to exacerbate the psychological effects of the disease. Because of the impact of obesity on individuals and society, much effort has been expended to find ways to treat obesity, but little success has been achieved in the long-term treatment and/or prevention of obesity.

Obesity represents the most prevalent of body weight disorders, and it is the most important nutritional disorder in the western world, with estimates of its prevalence ranging from 30% to 50% within the middle-aged population. Obesity, defined as an excess of body fat relative to lean body mass, also contributes to other diseases. For example, this disorder is responsible for increased incidence of diseases such as coronary artery disease, hypertension, stroke, diabetes, hyperlipidemia, and some cancers. Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity. The epidemiology of obesity strongly shows that the disorder exhibits inherited characteristics.

In summary, therefore, obesity, which poses a major, worldwide health problem, represents a complex, highly heritable trait. Given the severity, prevalence, and potential heterogeneity of such disorders, there exists a great need for the identification of those genes that participate in the control of obesity, particularly so as to be able anticipate the risk of developing this pathology or pathology related to obesity and/or to develop better targeted medicaments. This is the object of the present invention.

Previous work identified a childhood obesity locus on chromosome 6q16.3-q24.2 (lod score=4.06)[1] that includes a 2.4 Mb type 2 diabetes/obesity-linked region common to all eight published genome scans reporting linkage in this region[1-8].

The present inventors have, by conducting genotype-phenotype association studies in the 580 kb ENPP1 region and ENPP1 mRNA expression studies in 3,147 French Caucasian and in more than 6,000 European subjects individuals.

The ENPP1 gene encodes the ecto-nucleotide pyrophosphatase/phosphodiesterase 1 (ENPP1) which is a member of the ecto-nucleotide pyrophosphatase/phosphodiesterase (ENPP) family. The encoded protein is a type II transmembrane glycoprotein comprising two identical disulfide-bonded subunits. This protein has broad specificity and cleaves a variety of substrates, including phosphodiester bonds of nucleotides and nucleotide sugars and pyrophosphate bonds of nucleotides and nucleotide sugars. This protein may function to hydrolyze nucleoside 5' triphosphates to their corresponding monophosphates and may also hydrolyze diadenosine polyphosphates. Mutations in this gene, particularly, have been associated with 'idiopathic' infantile arterial calcification (GLU893TER, ARG774CYS or LEU579PHE), ossification of the posterior longitudinal ligament of the spine (OPLL) (IVS20AS, 1-BP DEL,T,−11) and insulin resistance (LYS121GLN, the "K121Q" mutation).

The inventors have demonstrated a strongest association to be between variant of this ENPP1 gene, particularly a three allele risk haplotype (K121Q; IVS20 delT−11 and a SNP localized in the 3'UTR domain sequence (notably A>G +1044 TGA, QdelTG) and childhood obesity and adults with morbid obesity. The inventors have also demonstrated the presence of at least one allele of the risk haplotype was associated with increased serum levels of soluble ENPP1 protein in children suggesting additional elevated ENPP1 expression. In addition, expression of a long ENPP1 mRNA isoform comprising the obesity-associated A>G +1044 TGA SNP was found to be specific for three tissues of major importance for glucose homeostasis: the pancreatic islet β-cells, adipocytes and liver. These findings demonstrate for the first time a primary role for several variants of ENPP1 in mediating insulin-resistance, both in the development of obesity and type 2 diabetes (T2D), providing common molecular mechanism of both widespread afflictions.

The inventors have also provided screening assays which can be used to diagnostic the risk of developing obesity and/or pathology related to obesity and to identify molecules for therapeutic treatment.

So, in a first aspect, the present invention is directed to a method for determining if a subject is at increased risk to develop obesity or pathology related to obesity from a biological sample from said subject containing genomic DNA or RNA, said method comprising the steps of:

a) determining on at least one gene allele or RNA sequence encoding the protein ENPP1, if said nucleic sequence, or fragments thereof, contains at least one SNP selected from the group of SNPs consisting of the SNPs indicated in table 3 and wherein the variant allele frequency is superior to 5%; and b) observing whether or not the subject is at increased risk to develop obesity or pathology related to obesity by observing if said sequence, or fragments thereof, contains said at least one SNP, the presence of said SNP indicates said subject is at increased risk to develop obesity or pathology related to obesity.

In a preferred embodiment, the present invention encompasses a method for determining if a subject is at increased risk to develop obesity or pathology related to obesity from a biological sample from said subject containing genomic DNA or RNA, said method comprising the steps of:

a) determining on at least one gene allele or RNA sequence encoding the protein ENPP1, if said nucleic sequence, or fragments thereof, contains at least one SNP selected from the group of SNPs consisting of IVS2 delG +8, K121Q, IVS8 T>G +27, IVS20 delT −11, A>G +1044 TGA and T>G +5954 TGA; and b) observing whether or not the subject is at increased risk to develop obesity or pathology related to obesity by observing if said sequence, or fragments thereof, contains said at least one SNP, the presence of said SNP indicates said subject is at increased risk to develop obesity or pathology related to obesity.

In a second aspect, the present invention is directed to a method for determining if a subject is at increased risk to develop obesity or pathology related to obesity from a biological sample from said subject containing genomic DNA or RNA, said method comprising the steps of:

a) determining on at least one gene allele or RNA sequence encoding the protein ENPP1, if said nucleic sequence, or fragments thereof, contains the haplotype comprising the three following SNPs:
K121Q (rs1044498),
IVS20 delT–11, and
a SNP localized in the 3'UTR domain sequence; and b) observing whether or not the subject is at increased risk to develop obesity or pathology related to obesity by observing if said sequence, or fragments thereof, contains said haplotype, the presence of said haplotype indicates said subject is at increased risk to develop obesity or pathology related to obesity.

In the present description, the term "rs" for example in the wording "rs1044498" corresponds to the nomenclature of the SNP in the databank dbSNP.

The SNP "K121Q (rs1044498)" is intended to designate the SNP rs1044498 corresponding to the ENPP1 variant "K121Q" (121 is the amino acid position in the ENPP1 amino acid sequence having the accession number (A.N.) NP_006199 (SEQ ID No. 14), which corresponds to the position 173 in the ENPP1 amino acid sequence having the accession number AAH159375. The accession number BC059375 corresponds to the mRNA nucleotide sequence encoding the human ENPP1 protein having the sequence depicted under A.N. AAH159375).

The SNP "IVS20 delT–11" correspond to the position –11 before exon 21 of ENNP1 as shown below:
Aaaaattagccaggcgtggtgggtca-
cacctgtaatcccagcactttgaggggctgcagcggatggatcacctgaggtca
ggagctcaagaccagccttgccaacatg-
gtgaaacccccatctctaccaaaaacacaaaaattagccaggcgtggtggcagat
gcctgtagtcccagctactcgggaagct-
gaggcaggagaatcgcttgaacctgggggggcagagttgcggtgagccgagatt
gcgccgctgccctctagtctgggtgaca-
gagtgagactccatcttaaaaaaataataataataataaataaataaataaataaataaat
atttaaaattgtgtagataaaatcat-
tctaaacattatttcatattagcatag-
cagaatctgaaaatatttgcataaatatgacaattaat atctttaatattgtaaag-
catttttacactttagttagaaaaaaagatgaatatactagtaggaaaatagggaaggacatgagctga cagctagagatcataattttatgatg-
tagttcacctttaaatattaataaag-
caAttttcttctctgtgcctgatatctgagagttcttc tcatttt(delT)cgttcttcag-
GACAGTTTCTCTACGGAAGACTTCTCCAACTGT
CTGTAC CAGGACTTTAGAATTCCTCTTAGTCCT-
GTCCATAAATGTTCATTTTATAAAA ATAACAC-
CAAAGTGAGTTACGGGTTCCTCTC-
CCCACCACgtaagttttttcctctcctgacc
ttccctttctccttttgttttctttcttgtttataaatcctaccatacattatagggtaat (SEQ ID No: 1).

The term "haplotype" refers to a combination of alleles present in an individual or a sample. In the context of the present invention a haplotype preferably refers to a combination of polymorphism alleles found in a given individual and which may be associated with a phenotype.

The term "polymorphism" as used herein refers to the occurrence of two or more alternative genomic sequences or alleles between or among different genomes or individuals.

"Polymorphic" refers to the condition in which two or more variants of a specific genomic sequence can be found in a population. A "polymorphic site" is the locus at which the variation occurs. A "single nucleotide polymorphism" (SNP) is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms.

Variant nucleic will be understood to mean all the alternative nucleic sequence which may naturally exist, in particular in human beings, and which correspond in particular to deletions, substitutions and/or additions of nucleotides. In the present case, the variant nucleic sequence will be in particular partly associated with the increased risk to develop obesity or pathology related to obesity.

As used interchangeably herein, the terms "oligonucleotides", "nucleic acids" and "polynucleotides" include RNA, DNA, or RNA/DNA hybrid sequences of more than one nucleotide in either single chain or duplex form.

As used herein, the term "nucleic acids" and "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule. Also, used interchangeably herein are terms "nucleic acids", "oligonucleotides", and "polynucleotides".

In a preferred embodiment, said pathology related to obesity is selected from the group consisting of type 2 diabetes, heart disease, coronary artery disease, myocardial infarct, hypertension and lipid related metabolic such as hypercholesterolemia and hyperlipidemia.

In a more preferred embodiment, said pathology related to obesity is type 2 diabetes (T2D).

Concerning said SNP which is localized in the 3'UTR domain sequence, it is preferred that this SNP is selected from the group of SNPs consisting of A>G +1044 TGA (rs7754561), A>C +1092 TGA (rs7754586), C>T +1157 TGA (rs7754859), G>T +1101 TGA, T>C +1137 TGA C>T +1157 TGA, G>T +1236 TGA, T>C +1348 TGA, G>A +1350 TGA, A>G +1539 TGA and T>C +1670 TGA. More preferred is a SNP selected from the group consisting of A>G +1044 TGA, A>C +1092 TGA and C>T +1157 TGA, and the SNP A>G +1044 TGA localized in the 3'UTR domain being the most preferred.

Is also preferred a method for determining if a subject is at high increased risk to develop obesity or pathology related to obesity, characterized in that said method comprises the step a) and b) of the above method according to the invention wherein:

in step a), it is determined whether or not the subject is homozygous for said haplotype comprising said three SNPs; and in step b), it is observed whether or not the subject is at height increased risk to develop obesity or pathology related to obesity by observing if the subject is homozygous for said haplotype, the homozygosity indicating said subject is at high increased risk to develop obesity or pathology related to obesity.

The methods allowing the detection of variation in a gene compared with the natural gene are, of course, highly numerous. They can essentially be divided into two large categories. The first type of method is that in which the presence of a variation is detected by comparing the alternative sequence with the corresponding normal sequence(s), and the second type is that in which the presence of the variation is detected indirectly, for example by evidence of the mismatches due to the presence of the variation.

Among the methods for the determination of an allelic variability, the methods comprising at least one stage for the so-called PCR (polymerase chain reaction) or PCR-like amplification of the target sequence comprising the three allele risk haplotype according to the invention with the aid of a pair of primers of nucleotide sequences according to the invention are preferred. The amplified products may be treated with the aid of an appropriate restriction enzyme before carrying out the detection or assay of the targeted product.

PCR-like will be understood to mean all methods using direct or indirect reproductions of nucleic acid sequences, or alternatively in which the labeling systems have been amplified, these techniques are of course known, in general they involve the amplification of DNA by a polymerase; when the original sample is an RNA, it is advisable to carry out a reverse transcription beforehand. There are currently a great number of methods allowing this amplification, for example the so-called NASBA "Nucleic Acid Sequence Based Amplification", TAS "Transcription based Amplification System", LCR "Ligase Chain Reaction", "Endo Run Amplification" (ERA), "Cycling Probe Reaction" (CPR), and SDA "Strand Displacement Amplification", methods well known to persons skilled in the art.

So, also forms part of the present invention a method for determining if a subject is at (high) increased risk to develop obesity or pathology related to obesity according to the invention, wherein the step a) of determining the presence or absence of said three allele risk haplotypes is carried out by a method comprising a step of amplification of the genomic DNA or RNA sequence, preferably DNA sequence, or fragments thereof, susceptible to contain said haplotype SNPs by polymerase chain reaction (PCR).

In said method wherein the step a) of determining the presence or absence of the three allele risk haplotypes is carried out by a method comprising a step of amplification PCR, the primers used can be all the primers which may be deduced from the nucleotide sequence of the ENPP1 gene and which may make it possible to detect the presence of said haplotype containing or consisting of the three SNPs K121Q, IVS20 delT−11 and a SNP localized in the 3'UTR domain sequence (the first 1170 bp 3'UTR domain wild type sequence (including the TGA codon) having the sequence SEQ ID No. 15).

The term "primer" denotes a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase or reverse transcriptase.

The primers which can be used for the method of the present invention may be designed from the disclosed sequences for any method known in the art. A preferred set of primers is fashioned such that the 3' end of the contiguous span of identity with the target sequence is present at the 3' end of the primer. Such a configuration allows the 3' end of the primer to hybridize to the selected nucleic acid sequence.

Allele specific primers may be designed such that a polymorphism is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a polymorphism.

In a preferred embodiment, said method for determining if a subject is at (high) increased risk to develop obesity or pathology related to obesity according to the invention is characterized in that the step of PCR is carried out from genomic DNA, mRNA or cDNA, eventually after a step of reverse transcription, or fragments thereof, by using the following sets of primers:

a) 5'-TCATACTCAGGAAGACAGCAA-3' (forward primer SEQ ID No. 2) and 5'-CAATAGCCATGACTC-CTAA-3' (reverse primer SEQ ID No. 3) for "K121Q" SNP;

b) 5'-AGCATTTTTACACTTTAGTT-3' (forward primer SEQ ID No. 4) and 5'-ATAATGTATGGTAGGATTT-3' (reverse primer SEQ ID No. 5) for IVS20 del T −11 SNP; and c) 5'-ATATTCCTATCCTGCTCACT-3' (forward primer SEQ ID No. 6) and 5'-TGCAGCTGGCCCTTAGGCCG-3' (reverse primer SEQ ID No. 7) for A>G +1044 TGA SNP.

In a particular embodiment, said method for determining if a subject is at (high) increased risk to develop obesity or pathology related to obesity according to the invention is characterized in that the step of PCR is carried out from genomic DNA, mRNA or cDNA, eventually after a step of reverse transcription, or fragments thereof, by using the two following sets of primers:

a) -5'-CTTTCCCCAATCACTACAGCATTGTCA-3' (forward primer, exon 7, SEQ ID No. 8), and
   -5'-TTTCAGACCATCCATCAGCATACCAAC-3' (reverse primer exon 12, SEQ ID No. 9); and for the 3'UTR SNP b) -5'-GTCCTGTGTTTGACTTTGATTATGA-3' (forward primer exon 23, SEQ ID No. 10), and
   -5'-CCCTTAGGCCGTTGAAGAATGGTCA-3'(reverse primer 3'UTR, SEQ ID No. 11).

In an also preferred embodiment, said method for determining if a subject is at (high) increased risk to develop obesity or pathology related to obesity according to the invention is characterized in that said biological sample is a sample of liver, adipocytes or pancreatic beta-cells when the presence of said haplotype is determined on RNA sequence or fragments thereof.

Still further embodiments of the invention concern methods for determining if a subject is at increased risk to develop obesity or pathology related to obesity from a plasma or serum sample from said subject, said method comprising the steps of:

a) determining the concentration of the serum or plasma ENPP1 protein; and b) observing whether or not the subject is at increased risk to develop obesity or pathology related to obesity by observing if said concentration is significantly higher than the level of normal, the presence of said significantly higher concentration indicates said subject is at increased risk to develop obesity or pathology related to obesity.

In a preferred embodiment, higher significant concentration of serum or plasma ENPP1 protein corresponds to at least more than 10%, preferably more than 15% of the normal serum or plasma concentration.

This invention further pertains to methods for determining if a subject is at increased risk to develop obesity or pathology related to obesity from a plasma or serum sample from said subject, according to the invention, wherein said concentration of serum or plasma ENPP1 protein is determined by using antibodies capable of specifically recognizing the ENPP1 protein or a specific epitopic fragment thereof.

In a preferred embodiment, said method is characterized in that said antibodies are brought into contact with the serum or plasma to be tested, under conditions allowing the formation of a specific immunological complex between the ENPP1 protein and said antibody, and in that the immunological complexes formed is quantified.

Other aspects encompass a method for determining if a subject is at increased risk to develop obesity or pathology related to obesity from a plasma or serum sample from said subject and from a biological sample containing a genomic DNA or RNA sequence, or fragments thereof, susceptible to contain the ENPP1 gene three allele risk haplotypes, said method comprising the determination of serum or plasma ENPP1 protein concentration and the observation whether said is serum or plasma ENPP1 protein concentration is significantly higher than the level of normal, and whether said DNA or RNA sequence contains the three allele risk haplotype.

In a preferred embodiment for these methods for determining if a subject is at increased (height) risk to develop obesity or pathology related to obesity, the pathology related to obesity is selected from the group consisting of type 2 diabetes, hypertension, hypercholestrolemia and hyperlipidemia particularly type 2 diabetes.

In another aspect, the present invention also encompasses a kit for determining if a subject is at increased risk to develop obesity or pathology related to obesity comprising one or more primers or set of primers, or probes, optionally with a portion or all of the necessary reagents and instructions for genotyping a test subject by determining the identity of a nucleotide at the three following SNPs of the ENPP1 region:
K121Q,
IVS20 delT−11, and
a SNP localized in the 3'UTR domain sequence.

The primers or the probes of said kit may optionally be attached to a solid support, or be part of an array or addressable array of polynucleotides. The kit may provide for the determination of the identity of the nucleotide at these three SNPs of the ENPP1 region position by any method known in the art including, but not limited to, a sequencing assay method, a microsequencing assay method, a hybridization assay method, an allele specific amplification method, or a mismatch detection assay based on polymerases and/or ligases chain reaction.

In a preferred embodiment, said kit for determining if a subject is at increased risk to develop obesity or pathology related to obesity, comprising at least one pair of primers or a set of a pair of primers capable of amplifying a fragment of genomic DNA or RNA encoding the protein ENPP1 and susceptible of containing the haplotype comprising the three following SNPs:
K121Q,
IVS20 delT−11, and
a SNP localized in the 3'UTR domain sequence.

In a more preferred embodiment for said kit, the SNP localized in the 3'UTR domain is selected from the group of SNPs consisting of A>G +1044 TGA, A>C +1092 TGA, G>T +1101 TGA, T>C +1137 TGA, C>T +1157 TGA, G>T +1236 TGA, T>C +1348 TGA, G>A +1350 TGA, A>G +1539 TGA and T>C +1670 TGA. Further more preferred for said kit is the SNP localized in the 3'UTR domain is selected from the group of SNPs consisting of A>G +1044 TGA, A>C +1092 TGA and C>T +1157 TGA, the group A>G +1044 TGA and A>C +1092 TGA SNP being also preferred, and A>G +1044 TGA being the most preferred.

In a particular embodiment, the invention encompasses a kit for determining if a subject is at increased risk to develop obesity or pathology related to obesity according to the present invention wherein said at least set of a pair of primers is:
  a) 5'-TCATACTCAGGAAGACAGCAA-3' (forward primer SEQ ID No. 2) and 5'-CAATAGCCATGACTC-CTAA-3' (reverse primer SEQ ID No. 3) for "K121Q" SNP;
  b) 5'-AGCATTTTTACACTTTAGTT-3' (forward primer SEQ ID No. 4) and 5'-ATAATGTATGGTAGGATTT-3' (reverse primer SEQ ID No. 5) for IVS20 del T −11 SNP; and
  c) 5'-ATATTCCTATCCTGCTCACT-3' (forward primer SEQ ID No. 6) and 5'-TGCAGCTGGCCCTTAGGCCG-3' (reverse primer SEQ ID No. 7) for A>G +1044 TGA SNP.

In another particular embodiment, the invention encompasses a kit for determining if a subject is at increased risk to develop obesity or pathology related to obesity according to the present invention wherein said at least set of a pair of primers is:
  a) -5'-CTTTCCCCAATCACTACAGCATTGTCA-3' (forward primer, exon 7, SEQ ID No. 8), and
    -5'-TTTCAGACCATCCATCAGCATACCAAC-3' (reverse primer exon 12, SEQ ID No. 9); and for the 3'UTR SNP;
  b) -5'-GTCCTGTGTTTGACTTTGATTATGA-3' (forward primer exon 23, SEQ ID No. 10), and
    -5'-CCCTTAGGCCGTTGAAGAATGGTCA-3' (reverse primer 3'UTR, SEQ ID No. 11).

In another aspect, the present invention is directed to an isolated variant nucleic sequence, or to an isolated nucleic acid molecule, or complementary sequence thereof, of a mammal, preferably human, genomic DNA or RNA sequence of the gene coding for ENPP1 protein, characterized in that said isolated variant nucleic sequence comprises the haplotype comprising the three SNPs as defined above K121Q, IVS20 delT−11 and a SNP localized in the 3'UTR domain sequence such as one of the SNPs selected from the group of SNPs consisting of A>G +1044 TGA, A>C +1092 TGA, G>T +1101 TGA, T>C +1137 TGA, C>T +1157 TGA, G>T +1236 TGA, T>C +1348 TGA, G>A +1350 TGA, A>G +1539 TGA and T>C +1670 TGA. The A>G +1044 TGA or A>C +1092 TGA SNP being the more preferred of the SNPs localized in the 3'UTR domain sequence and the SNP A>G +1044 TGA being the most preferred.

An "isolated" nucleic acid sequence or molecule is one which is separated from other nucleic acid sequences or molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the subject from which the nucleic acid is derived. For example, in various embodiments, the isolated variant nucleic sequence of the invention can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule of the present invention, can be isolated using standard molecular biology techniques and the sequence information provided herein. Using all or a portion of the ENPP1 variant nucleic acid sequence which comprises the haplotype comprising the three SNPs as defined above K121Q, IVS20 delT−11 and a SNP localized in the 3'UTR, the isolated nucleic acid molecules of the present invention can be isolated using standard hybridization and cloning techniques (e.g., as described in Sambrook, J., Fritsh, E. F., and Maniatis, T. Molecular Cloning. A Laboratory Manual., 2nd, ed., Cold Spring Harbor Laboratory, Cold Spring Harbor Laboratory Press, Cold Spring Harbor, N.Y., 1989).

Another aspect of the invention pertains to vectors, preferably expression vectors, containing a nucleic acid encoding the isolated variant nucleic sequence of ENPP1 of the present invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention can comprise the isolated variant nucleic sequence of the gene coding for ENPP1 protein of the present invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). The expression vectors of the invention such as yeast expression vector or baculovirus expression vectors, can be introduced into host cells, in prokaryotic or eukaryotic cell, to thereby produce proteins or peptides. In another embodiment, the expression vector of the present invention is capable of directing expression of the nucleic acid preferentially in mammalian cells or in a particular cell type (e.g., tissue-specific regulatory elements are used to express the nucleic acid).

Another aspect of the invention pertains to host cells into which a recombinant expression vector of the invention has been introduced. The terms "host cell" and "recombinant host cell" are used interchangeably herein. It is understood that such term refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the isolated ENPP1 variant nucleic sequence of the present invention can be expressed in bacterial cells such as *E. coli*, insect cells, yeast or mammalian cells (such as Chinese hamster ovary cells (CHO) or COS cells or human cells). Other suitable host cells are known to those skilled in the art, including *Xenopus laevis* oocytes.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs.

The host cells of the invention can also be used to produce non-human transgenic animals. For example, in one embodiment, a host cell of the invention is a fertilized oocyte or an embryonic stem cell into which the isolated ENPP1 variant nucleic sequence of the present invention have been introduced. Such host cells can then be used to create non-human transgenic animals in which exogenous ENPP1 variant nucleic sequence of the present invention have been introduced into their genome or homologous recombinant animals in which endogenous ENPP1 nucleic sequence have been altered in order to insert the haplotype variant of the present invention. Such animals are useful for studying the function and/or activity of ENPP1 polypeptide or fragment thereof and for identifying and/or evaluating modulators of ENPP 1. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ENPP1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing the ENPP1 variant nucleic acid of the present invention into the male pronuclei of a fertilized oocyte, e.g., by microinjection or retroviral infection, and allowing the oocyte to develop in a pseudopregnant female foster animal. Alternatively, a nonhuman homologue of the human ENPP1 gene variant of the present invention, such as a mouse or rat ENPP1 gene variant, can be used as a transgene. Methods for generating transgenic animals via embryo manipulation and microinjection, particularly animals such as mice, have become conventional in the art and are well described.

To create an animal in which a desired nucleic acid has been introduced into the genome via homologous recombination, a vector is prepared which contains at least a portion of a ENPP1 gene into which the at least three mutation of the haplotype of the present invention has been introduced to thereby alter the ENPP1 gene.

So, the present invention relates to transgenic mammal, except human, characterized in that it comprises a transformed cell according to the invention or a cell containing a recombinant functional ENPP1 gene comprising at least the haplotype comprising the three SNPs as defined above (K121Q; IVS20 delT-11 and a SNP localized in the 3'UTR domain sequence).

In another aspect, the invention comprises the use of cell or a transgenic mammal according to the present invention, for screening chemical or biochemical compounds for the treatment or the prevention of obesity or pathology related to obesity.

In a preferred embodiment, said method for selecting a chemical or biochemical compound for the treatment or the prevention of obesity or pathology related to obesity is characterized in that it comprises the step of:
 a) bringing into contact a transformed cell or a transgenic mammal according to the invention with said chemical or biochemical compound to be tested; and
 b) observing whether the expression product of the ENPP1 gene is decreased or not in said cell or said mammal.

In a more preferred embodiment, said method for selecting a chemical or biochemical compound for the treatment or the prevention of obesity or pathology related to obesity according to the present invention is characterized in that:
 in step a), the chemical or biochemical compound to be tested is administered to a transgenic mammal to the present invention or to a transgenic mammal overexpressing the ENPP1 protein; and
 in step b), it is observed whether the serum or plasma ENPP1 protein concentration is decreased compared to a reference,
 said chemical or biochemical compound being selected if a decrease of said concentration is observed.

In another aspect, the present invention is also directed to a method of determining the efficacy of a drug to reduce the risk of obesity or pathology related to obesity in a patient, comprising the steps of:
 (a) collecting a serum or plasma sample from said patient prior to and subsequent to administering said drug to said patient;
 (b) determining the serum or plasma ENPP1 protein concentration in said collected sample, wherein a decrease in the serum or plasma ENPP1 protein concentration subsequent to said treatment is indicative of a treatment that reduces the risk of obesity or pathology related to obesity.

EXAMPLES

Several of the methods of the present invention are described in the following examples, which are offered by way of illustration and not by way of limitation. Many other modifications and variations of the invention as herein set forth can be made without departing from the spirit and scope thereof.

Legends to Figures

FIG. 1. Pairwise LD between fifty-three SNPs in a 580 kb region including the ENPP1 gene in 421 obese children and 298 control individuals. Regions of high and low LD (delta) are presented by red and blue shading, respectively. The graph is to the physical map scale.

Figure 2:
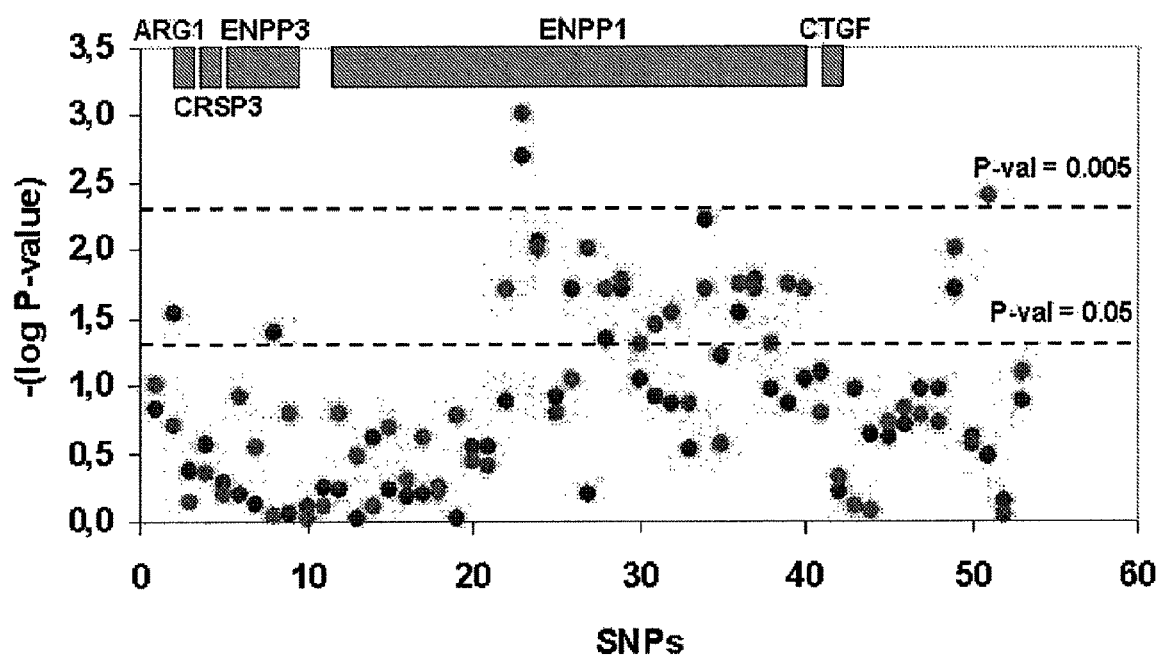

FIG. 2. Allelic association of fifty-three SNPs in the 580 kb region including the ARG1, CRSP3, ENPP3, ENPP1 and CTGF genes. Blue circles correspond to the $-\log_{10}$ (p-value) for the comparison of allelic distribution between 421 obese children and 298 control individuals. Red circles correspond to the $-\log_{10}$ (p-value) for the comparison of allelic distribution between 62 "6q-evidence" families obese children and 298 control individuals. The figure is not to scale according to the physical map location; indeed the SNPs are equidistant to allow easy visualization of the association test results.

Figure 3:
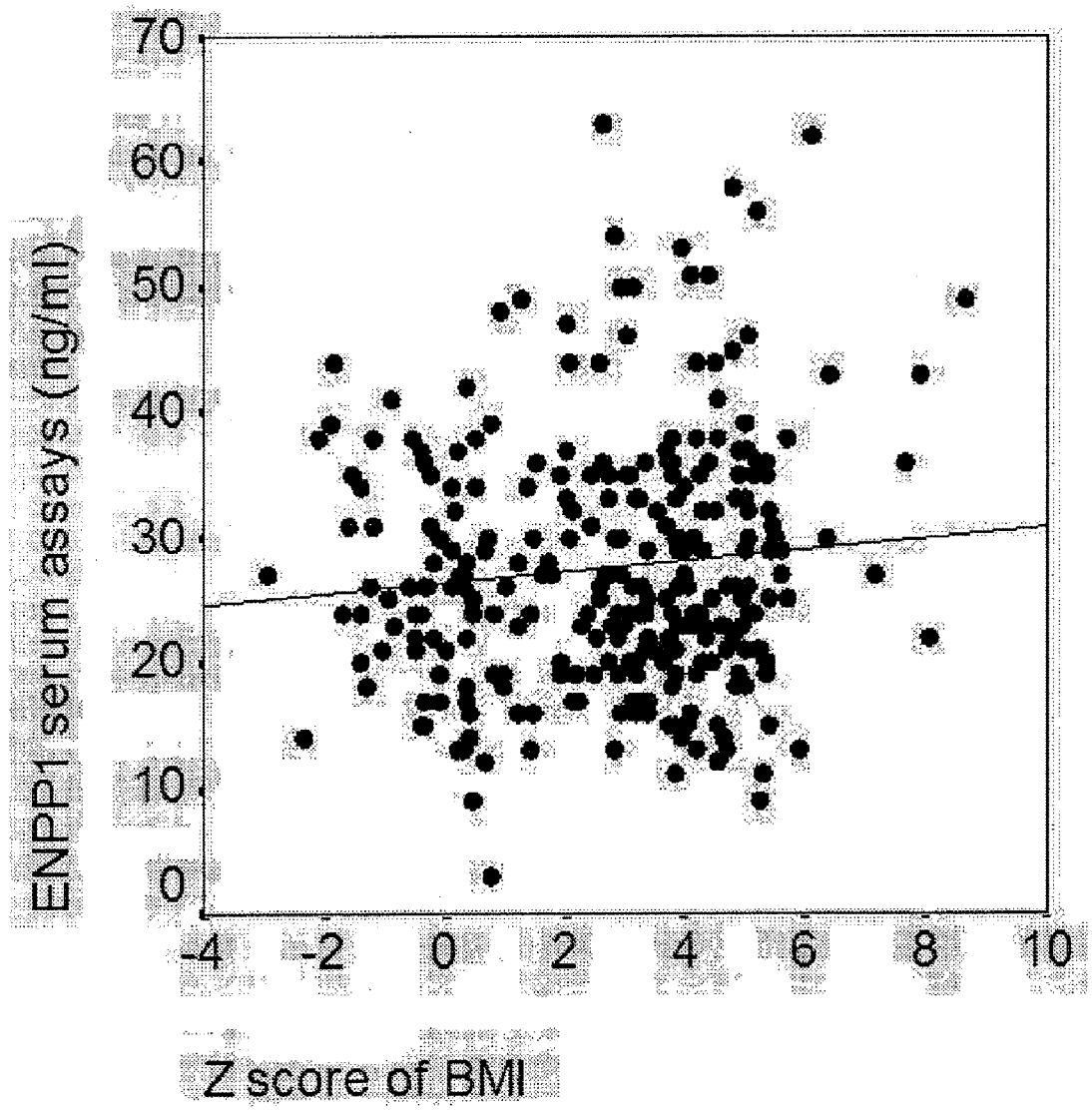

FIG. 3. Correlation of the ENPP1 protein serum level with Z score of BMI in 279 children.

Figure 4:
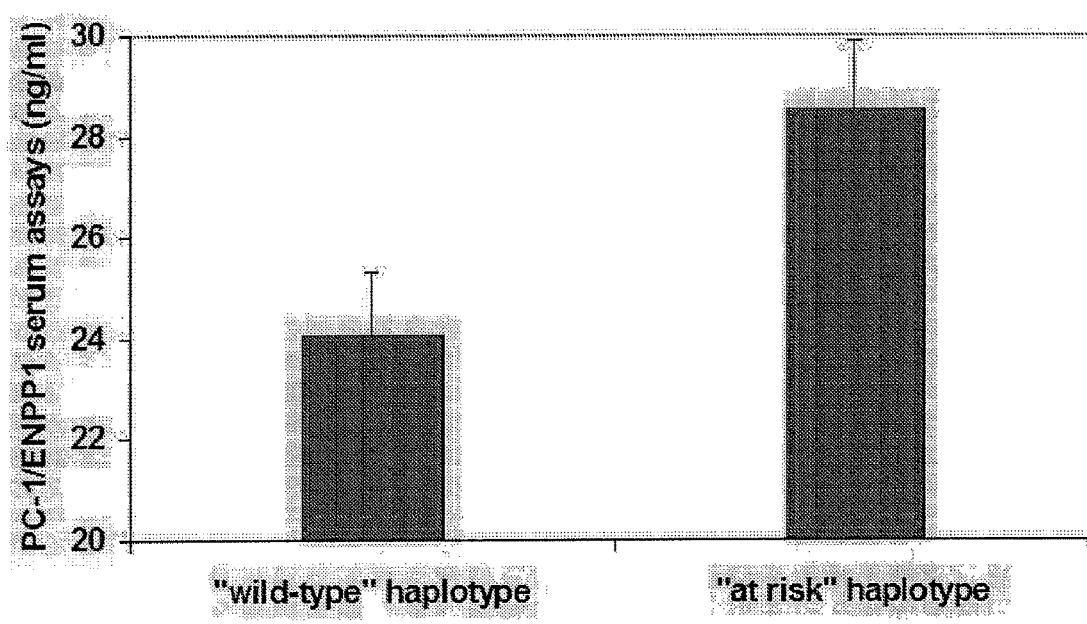

FIG. 4. ENPP1 serum level in 89 lean children according to the presence of the risk haplotype.

Figures 5A, 5B:
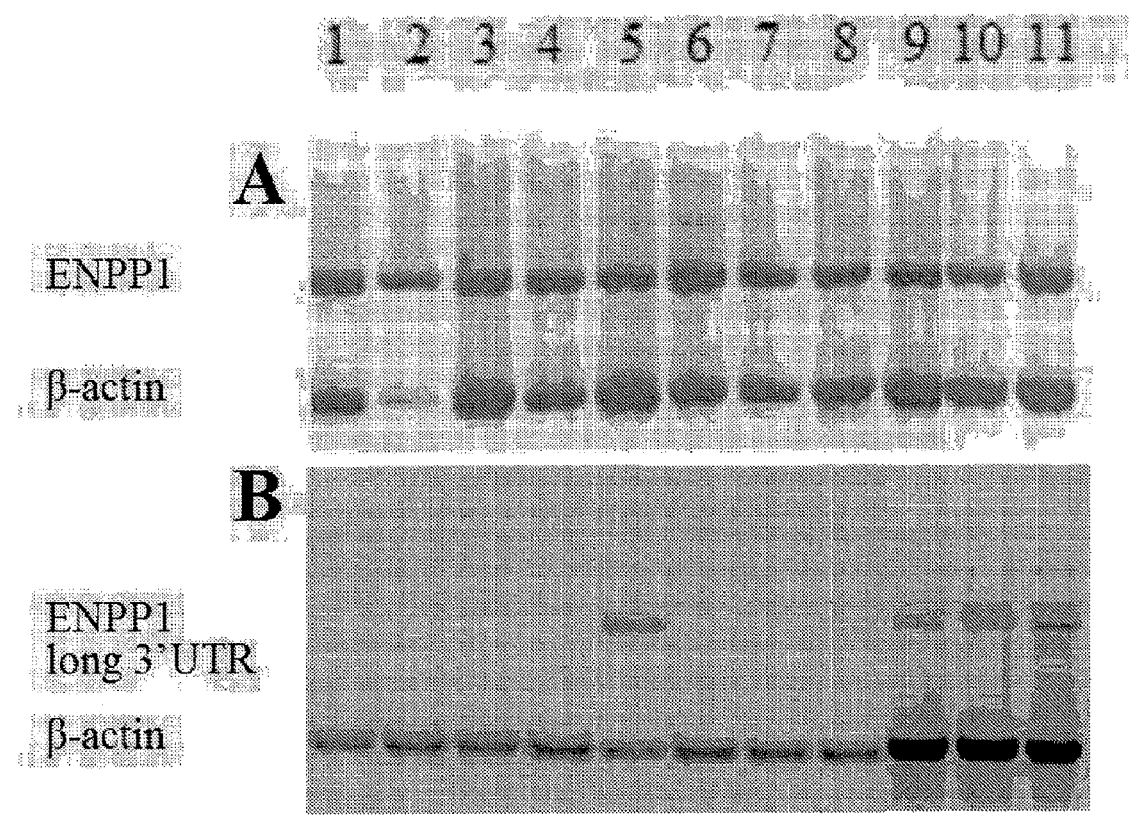

FIGS. 5A and 5B. mRNA expression of PC-1/ENPP1 in human tissues. PCR was performed to detect β-actin and ENPP1. Lane 1, Heart; 2 brain; 3, placenta; 4, lung; 5, liver; 6, skeletal muscle; 7, kidney; 8, pancreas (MTC panel) 9, human beta-cells; 10, subcutaneous adipocyte and 11, omental adipocyte. Taking into account that five ENPP1 isoforms were described in databases (http://www.ncbi.nih.gov/IEB/Research/Acembly/av.cgi?db=human&1=ENPP1), we first designed primers amplifying a coding region between exon 7 and 12 which is common to at least 3 transcripts, and found ubiquitous expression (FIG. 5A). We then designed primers specific to the long mRNA isoform, characterized by a larger 3'UTR (1,170 bases downstream the TGA, including the obesity-associated SNP A/G +1044 TGA) and found an expression specific to pancreas and beta-cells, subcutaneous and omental adipocyte and liver (FIG. 5B).

Example 1

Methods a) Subjects

Phenotypic characteristics and type of study performed on each sample are summarized in table 1.

TABLE 1

Description of the French and Austrian samples used in the study. Sex ratio: female/male

| Population | Effective | Age (y.) | BMI (kg/m²) | Sex ratio | Type of study |
|---|---|---|---|---|---|
| Obese children | N = 529 | 10.4 ± 3.9 | 28.2 ± 6.4 | 281/248 | Association, 6q linkage, TDT, phenotypes, serum |
| Parents of ob. ch. | N = 464 | 40.7 ± 5.8 | 31.4 ± 7.7 | 232/232 | Phenotypes |
| Morbidly obese | N = 696 | 45.8 ± 12.0 | 47.4 ± 7.4 | 520/176 | Association |
| Moderately obese | N = 717 | 49.1 ± 14.7 | 34.6 ± 4.0 | 401/316 | Association |
| Obese adults | N = 325 | 35.6 ± 12.1 | 32.3 ± 9.1 | 134/191 | TDT |
| French T2D | N = 752 | 59.3 ± 11.3 | 28.1 ± 4.3 | 379/373 | Association |
| Austrian T2D | N = 503 | 56.7 ± 10.2 | 30.4 ± 6.3 | 208/295 | Association |
| Lean children | N = 198 | 14.6 ± 2.2 | 18.3 ± 2.2 | 99/99 | Association, serum |
| Control 1 | N = 556 | 55 ± 6.0 | 22 ± 1.8 | 254/302 | Association |
| Control 2 | N = 649 | 50.9 ± 12.7 | 22.9 ± 2.3 | 394/255 | Association |
| Austrian control | N = 758 | 52.2 ± 5.8 | 26.8 ± 4.0 | 293/465 | Association |

Five hundred and twenty nine unrelated obese children were studied. We collected 336 pedigrees with at least one obese child at the CNRS-Institut Pasteur Unit and at the Jeanne de Flandres Hospital in Lille. One hundred and six additional obese children were recruited at the Children's Hospital, Toulouse, and 87 at the Trousseau Hospital, Paris. Children with a BMI greater than the 97$^{th}$ percentile of BMI for age and sex reported on the tables of Rolland-Cachera et al.[12] (French general population) were diagnosed as obese according to the recommendation of the European Childhood Obesity Group (ECOG)[42]. We used a set of 696 unrelated morbidly obese (BMI≧40 kg/m²) and 717 unrelated moderately obese (BMI between 30 and 40 kg/m²) adult patients. We also used for TDT 87 pedigrees with adult obesity (one proband with a BMI of greater than 40 kg/m², at least one additional sibling with a BMI of greater than 27 kg/m² and at least one parent). These individuals were collected at the Department of Nutrition of the Hôtel Dieu Hospital in Paris or at the CNRS-Institut Pasteur Unit in Lille. The 752 T2D subjects were recruited at the Sud Francilien Hospital in Corbeil-Essonnes or at the CNRS-Institut Pasteur Unit in Lille. Glucose Intolerance and type 2 diabetes status were defined according to the WHO 1999 criteria. The first set of 556 control subjects was obtained from the SUVIMAX population[43]. The second set of 649 control individuals was recruited at the CNRS-Institut Pasteur Unit in Lille and through the "Fleurbaix-Laventie Ville Santé" study[44]. The set of 1,261 unrelated Austrian subjects is a random subset of a previously described population[45]. In order to justify the use of non-age matched controls and to confirm there was no age-cohort effect on SNP and haplotype frequencies, we genotyped the K121Q, IVS20 delT −11 and A>G +1044 TGA polymorphisms in 198 control children from the "Fleurbaix-Laventie Ville Santé" study[44] and found very concordant frequencies for the Q allele (13.8%) and the risk haplotype (7.8%) in comparison with control adults. The 458 control trios (2 parents and one lean child) were issued from the "Fleurbaix-Laventie Ville Santé" cohort. Informed written consent was obtained from all the subjects before participation. The genetic study was approved by the Ethical Committee of Hotel Dieu in Paris and CHRU in Lille. The Z score of BMI was obtained according to Cole's method[46]. During oral glucose tolerance test (OGTT), subjects received after a 12 h overnight fast: 1) 1 g glucose/kg if subject's weight lower than 50 kg; 2) 75 g glucose if subject's weight higher than 50 kg. Blood samples were taken at 0, 30, 60, 90 and 120 min for the measurement of plasma glucose and insulin concentrations. Quantitative measurements of plasma insulin were carried out using double-antibody radioimmunoassays. Serum glucose concentrations were measured using a glucose oxidase procedure. Insulinogenic index was calculated according to Seltzer et al.[47].

b) Linkage Analysis

In sixty-eight nuclear families, comprising 306 individuals, five polymorphic markers (D6S1720, D6S434, D6S287, D6S1656, D6S292) covering the linkage interval of the initial genome-wide study[1] were used for genotyping. Two-point and multipoint analyses were performed using the MLS test[48] implemented in the GeneHunter software[49].

c) Mutation Screening

The twenty-five exons and UTRs (upstream 5' UTR and downstream 3' UTR) were screened using DHPLC (Transgenomic, San Jose, Calif., USA) in 48 unrelated obese children randomly selected among families contributing to the linkage at the chromosome 6q16-q24 locus and in 24 unrelated non-obese normoglycemic control subjects selected from French pedigrees. Variant profiles were sequenced using an automated ABI Prism 3700 DNA sequencer in combination with the Big Dye Terminator Cycle Sequencing Ready Reaction Kit (Applied Biosystems, Foster City, Calif., USA).

d) Genotyping

Genotyping of microsatellite markers was carried out using a fluorescence-based semi-automated technique on automated DNA sequencing machines (ABI 377, PE ABI). Primers were synthesized by MWG Biotech. SNPs were genotyped with the LightCycler™, LightTyper™ (Roche Diagnostics, Basel, Switzerland), with the TaqMan™ (Applied Biosystems, Foster City, Calif. USA) or by direct sequencing. Probes for LightCycler™ and LightTyper™ were synthesized by TIB Molbiol™ Syntheselabor Germany. For coverage of the 580 kb region, SNPs with an allele frequency>10% in Caucasians were selected using the Applied Biosystem SNP Viewer II software. In order to avoid SNP genotyping errors 10% of DNA samples were systematically re-genotyped for further verification. We found concordance rates of 100% for all SNPs.

e) Statistical Analyses

Comparison of allele frequencies between cases and controls was achieved using the $\chi^2$ test and the p value was empirically computed with the program CLUMP[50]. Haplotype frequencies were determined and were compared between groups with the UNPHASED software found on the World Wide Web at www.mrc-bsu.cam.ac.uldpersonal/frank/[51]. The effect of haplotypes on qualitative or quantitative trait variation was evaluated using the sub-programs cocaphase and qt-phase of UNPHASED software[51]. Independence of association was tested with the software THESIAS[32]. THESIAS also implements an EM algorithm and allows for likelihood testing of models of haplotype effect in a linear framework. We used this program to test whether the effect of each SNP, on the obesity status, was independent from the effect of K121Q alone. Haplotype analysis was preferred over multiple logistic regression as these SNPs were in partial LD. TDT analyses on SNPs and haplotypes were performed by the TDT method implemented in the UNPHASED software[51]. Because of low LD between the three SNPs of the risk haplotype, we only used the unambiguous haplotypes to obtain a true TDT robust to population stratification. In order to evaluate the effect of the risk haplotype on linkage, we used the Genotype IBD Sharing Test (GIST) procedure[23], which tests the correlation between the familial NPL score and an index of the risk haplotype frequency in the family.

f) Linkage Disequilibrium Analysis

LD (Linkage disequilibrium) among twenty-four identified ENPP1 SNPs and among fifty-three SNPs in the 580 kb ENPP1 region was investigated. Pairwise delta (correlation coefficient between SNPs) was estimated from genotypes and the results were visualized by the GOLD program (http://www.sph.umich.edu/csg/abecasis/GOLD/).

g) ENPP1 mRNA Expression

Human cDNAs from MTC Panel (BD Biosciences Contech), subcutaneous and omental adipocytes (provided by G Fruhbeck, university of Navarra Pamplona Spain) and FACS purified pancreatic beta cells (provided by the Human Pancreatic Cell Core Facility, University Hospital, Lille, France[52]) were used for mRNA expression analysis. The beta cell purity was confirmed by immunochemistry (98% insulin positive cells) and PCR (absence of amplification with chymotrypsin primers, specific for exocrine cells). PCR was performed in a 25 µl mixture containing 10 mM Tris-HCl, 1.5 mM MgCl2, 50 mMKCl, 10 mM of each dNTPs, 2.5 U of Taq polymerase (Promega), 30 mM of both forward primer and reverse primer, and 3 µl of single-strand cDNA. The forward primer for ENPP1 was (SEQ ID No. 8) 5'-CTTTCCCCAAT-CACTACAGCATTGTCA-3' (exon 7); and the reverse primer was (SEQ ID No. 9) 5'-TTTCAGACCATCCATCAGCAT-ACCAAC-3' (exon 12); and for beta-actin, a forward primer (SEQ ID No. 12: 5'-CGTCATACTCCTGCTTGCTGATC-CACATCTGC-3') and a reverse primer (SEQ ID No. 13: 5'-ATCTGGCACCACACCTTCTACAATGAGCTGCG-3') were used. The ENPP1 isoform, characterized by a larger 3'UTR (1170 bases downstream of the TGA stop codon) was amplified using SEQ ID No. 10 5'-GTCCTGT-GTTTGACTTTGATTATGA-3'(exon 23) and (SEQ ID No. 11 5'-CCCTTAGGCCGTTGAAGAATGGTCA-3' (3'UTR)). The mixtures were heated at 95° C. for 2 min and subjected to 45-cycle amplification at 95° C. for 30 s, 68° C. for 2 min., and 72° C. for 2 min, and then 10 min at 72° C. PCR products were separated on 2% (w/v) agarose gel and visualized using ethidium bromide and UV transillumination.

h) ENPP1 Protein Serum Assays

ENPP1 serum level was measured using the ELISA described by Rutsch et al.[24].

Example 2

Search for Positional Candidate Genes on Chromosome 6q16.3-q24.2

The phenotypic characteristics of 62 "6q-evidence" families (defined by an individual pedigree Gene Hunter Zscore>1.0 in the 2-LOD drop interval flanked by the microsatellite markers D6S434 and D6S1704) were first compared with the remaining 35 families, all issued from our previously published genome scan for childhood obesity[1].

TABLE 2

Phenotypic characteristics of "6q-evidence" families

| Trait | Obese children from "6q-evidence" families | Obese children from other families | p-value of the T-test or Chi2 test |
|---|---|---|---|
| Age | 11.52 ± 3.15 (N = 138) | 11.54 ± 3.41 (N = 70) | 0.95 |
| Gender (M/F) | 63/75 (N = 138) | 40/30 (N = 70) | 0.11 |
| ZBMI | 4.20 ± 0.11 (N = 138) | 3.74 ± 0.11 (N = 70) | 0.004 |
| AUGC | 773.04 ± 17.32 (N = 95) | 709.71 ± 17.30 (N = 50) | 0.07 |
| Ins Ind | 25.44 ± 3.01 (N = 71) | 41.33 ± 7.67 (N = 30) | 0.02 |
| % IG/T2D | 3.1% (N = 131) | 0% (N = 69) | 0.18 |
| Trait | Parents from "6q-evidence" families | Parents from other families | p-value of the Chi2 test |
| % T2D | 13.8% (N = 123) | 3.2% (N = 62) | 0.018 |

ZBMI: Z score of BMI. AUGC: area under the glycemia curve during 2 h oral glucose tolerance test. Ins Ind: Insulinogenic Index (mU·mmol$^{-1}$). % IG/T2D: percentage of obese children displaying glucose intolerance or type 2 diabetes mellitus. % T2D: percentage of parents displaying type 2 diabetes mellitus.

As shown in Table 2, the "6q-evidence" obese children have a significantly higher Z score of BMI (deviation of the body mass index compared to a French reference population[12]). After adjustment of parameters for sex, age and BMI, their blood glucose levels after glucose administration is higher, and their insulinogenic index, which estimates the first-phase insulin secretion, is significantly lower than in children of other families. Moreover, 3.1% of the "6q-evidence" obese children are either glucose intolerant or diabetic: in contrast, none of the obese children in other families is glucose intolerant. We also investigated the previous generation, and found that 13.8% of 6q linked parents have type 2 diabetes mellitus (T2D) as compared to 3.2% of parents in other families (p=0.02). These data led us to conclude that the obesity susceptibility gene(s) on chromosome 6q may be also involved in glucose homeostasis.

Based on our genome scan for childhood obesity[1] the 2-LOD drop interval for the 6q16.3-q24.2 linkage peak covers 41.4 Mb and includes 166 referenced genes. In order to focus the search for obesity susceptibility genes to a more restricted chromosomal area, the peaks of 7 published reports of linkage on chromosome 6q16.1-q27 with either obesity[2], insulin secretion[3,4] or T2D[5-8], all performed in adults, were analyzed. A 2.4 Mb interval was identified as common to all of the genome scans, spanning the region between markers D6S1656 and D6S270. Among the twenty two genes mapping within this interval, the best physiological candidate was ectonucleotide pyrophosphatase/phosphodiesterase ENPP1 (also known as the Plasma Cell glycoprotein-1 PC-1) (OMIM reference 173335). ENPP1 is believed to directly inhibit insulin-induced conformational changes of the insulin receptor, thereby affecting its activation and downstream signaling[9,13]. In this regard, a functional missense mutation (K121Q), which was proposed to more effectively inhibit insulin signalling[11], was associated with insulin resistance or T2D in various ethnic groups[14-18].

The microsatellite marker D6S1656 in intron 1 of the ENPP1 gene, linked to childhood obesity in our initial genome scan, was analyzed in a second replication set of 68 families having at least two sibs with BMI>95$^{th}$ percentile (corrected for gender and age) and modest evidence of linkage (MLS=0.83, p=0.04) was observed. In contrast, no linkage with obesity was found with 4 other microsatellite markers of this region in the replication set (data not shown). Allele 10 of D6S1656 was also significantly under-transmitted to affected children in both the initial and replication sets (44 transmitted vs 69 untransmitted, p=0.02, data not shown). These results suggested that functional polymorphisms in partial linkage disequilibrium (LD) may be located nearby.

Example 3

Sequence Variation within the ENPP1 Gene and Association with Obesity Due to ENPP1 SNPs ENPP1 has 25 exons and spans over 83.2 Kb. In order to characterise sequence variation within the gene, sequencing of all coding regions, and 1.3 Kb upstream of the ATG start codon and downstream of the TGA stop codon was carried out in 48 obese children from "6q-evidence" families and in 24 non-obese adults. Eight single-nucleotide polymorphisms (SNPs) were identified in the upstream sequence, six in intron/exon junctions, four were missense, three were synonymous mutations and twenty were identified in the downstream sequence (see table 3).

TABLE 3

Polymorphisms in 5' and 3' proximal regions, exons and boundaries of ENPP1 gene

| SNP | Description | Variant allele frequency (%) |
|---|---|---|
| 1 | C > T −1125 ATG | 0.7 |
| 2 | T > C −931 ATG | 0.7 |
| 3 (rs1800949) | C > T −768 ATG | 20.7 |
| 4 | G > C −406 ATG | 0.7 |
| 5 | C > T −359 ATG | 1.4 |
| 6 | G > T −190 ATG | 7.7 |
| 7 (rs12212106) | C > G −187 ATG | 20.4 |
| 8 | C > T −165 ATG | 4.5 |
| 9 | IVS2 delG +8 | 6.8 |
| 10 (rs1044498) | K121Q | 16.9 |
| 11 | IVS5 T > G −20 | 2.8 |
| 12 | IVS7 T > G −28 | 0.7 |
| 13 (rs9493113) | IVS8 T > G +27 | 8.3 |
| 14 | IVS9 G > C +24 | 2.1 |
| 15 (rs9483347) | K387K | 0.7 |
| 16 | IVS20 delT −11 | 25.3 |
| 17 (rs7750837) | S650S | 0.7 |
| 18 | R722C | 1.5 |
| 19 (rs1805138) | T727N | 0.7 |
| 20 (rs8192683) | R834T | 0.7 |
| 21 (rs1804025) | A835A | 3.6 |
| 22 (rs1044548) | G > A +112 TGA | 7.6 |
| 23 (rs11964389) | G > C +121 TGA | 3.5 |
| 24 (rs1044558) | C > T +164 TGA | 7.6 |
| 25 | G > A +395 TGA | 7.8 |
| 26 (rs1044582) | T > A +457 TGA | 7.8 |
| 27 | InsAA DelT +700 TGA | 7.7 |
| 28 (rs12212882) | A > G +735 TGA | 4.2 |
| 29 | A > T +772 TGA | 8.4 |
| 30 | C > T +777 TGA | 7.7 |
| 31 | Ins 13bp +828 TGA | 4.2 |
| 32 (rs7754561) | A > G +1044 TGA | 26.1 |
| 33 (rs7754586) | A > C +1092 TGA | 21.6 |
| 34 (rs11154647) | G > T +1101 TGA | 5.9 |
| 35 (rs11154648) | T > C +1137 TGA | 6 |
| 36 (rs7754859) | C > T +1157 TGA | 27.6 |
| 37 (rs11154649) | G > T +1236 TGA | 6 |
| 38 (rs9483349) | T > C +1348 TGA | 3.6 |
| 39 (rs9493120) | G > A +1350 TGA | 7.1 |
| 40 (rs9493121) | A > G +1539 TGA | 7.1 |
| 41 (rs9493122) | T > C +1670 TGA | 4.3 |

Among these forty-one polymorphisms, twenty-four were present in the public databases and twenty-two of the variants had a minor allele frequency (MAF) higher than 5%. For the nineteen infrequent polymorphisms, their transmission was inspected within pedigrees. When the rare allele was present in unaffected sibs the variant was not investigated further (n=14). The remaining five rare SNPs did not show any significant association with obesity in case-control analyses (data not shown). Pairwise LD among the twenty-two most common SNPs, plus two others: SNP23 (3.5%), previously described as influencing mRNA stability[19] and a 13 bp insertion (SNP31, Ins 13 bp +828 TGA, prevalence 4.2%) was used to select a set of ten "haplotype tagging" SNPs to be typed in the whole set of samples.

To further enhance the chances of identifying functional SNPs, twenty-five fragments were identified that were more than 100 bp long, showing a high degree of homology (>70%) across *Fugu rubripes*, rat and human genomes and within the 198 Kb of intronic and 5' and 3' intergenic regions of the ENPP1 gene. These fragments were sequenced and a further eleven SNPs of MAF>5% were identified. These SNPs were initially used to genotype a test set of 421 obese children and 298 control individuals. One SNP in the 3' region of ENPP1 (T>G +5954 TGA) that showed a trend for association with childhood obesity (p<0.1) was added to the set of SNPs analyzed in the whole sample set.

Altogether, eleven SNPs were genotyped in 2,430 individuals, made up of 529 unrelated obese children, 696 unrelated morbidly obese adults, and 1,205 lean normoglycaemic adults. Lean adults were used as controls for both sets of cases because they demonstrated a long term resistance against obesity. As shown in Table 4, we observed associations between severe forms of obesity and six of the SNPs: IVS2 delG +8, K121Q, IVS8 T>G +27, IVS20 delT −11, A>G +1044 TGA and T>G +5954 TGA (see Table 4, 0.00008<p<0.03; 1.21>OR>1.37). The global p-value, assessed by $10^5$ permutations of the obesity status among individuals, was 0.001. Analysis of the pooled data identified the strongest association with severe forms of obesity of the K121Q SNP (OR=1.37, 95% confidence interval [1.17-1.61], p=0.00008). The odds ratio under a recessive model was increased at 3.29 [1.83-5.93] (p=0.00003) with a significant departure from the additive model (p=0.02).

To test this association further, 184 multiplex families were genotyped for this SNP. This set consisted of the 97 childhood obesity genome scan families plus 87 nuclear families with adult severe obesity, which showed linkage of serum leptin levels to chromosome 6q24[20]. Using the Transmission Disequilibrium Test (TDT) the 121 Q-allele was significantly over-transmitted to obese offspring (transmitted: 76, non-transmitted: 48, p=0.01), supporting the case-control result.

To confirm ENPP1 specificity for these associations, a total of fifty-three SNPs in the chromosome 6q region, spanning 580 kb and including the ARG1, CRSP3, ENPP3, ENPP1 and CTGF genes, were typed in the initial set of 421 obese children and 298 control individuals used above (average density: 1 SNP/10.9 kb). Using the GOLD software, three distinct regions of linkage disequilibrium (LD) were noted; the first one contained ARG1, CRSP3 and ENPP3, the second one ENPP1 alone, and the third the CTGF gene and 176 Kb of non coding region (FIG. 1). Comparison of the allelic distribution of the fifty-three SNPs between obese children and controls, and also between sixty-two "6q-evidence" obese children and controls revealed that eight SNPs were associated with both childhood obesity and "6q-evidence" childhood obesity (p<0.05). Seven of the eight SNPs (K121Q, Celera dbSNP hcV1207989, C>T +164 TGA, Celera dbSNP hcV1207974, A>G +1044 TGA, G>T +1101 TGA, C>T +1157 TGA) mapped within ENPP1 (FIG. 2). The eighth associated SNP was located in an intergenic region, 69 kb 3' of CTGF, and not located in a fragment showing a high degree of homology across *Fugu rubripes*, rodent and human genomes and with no known transcription factor binding site. These data support the hypothesis that the observed association with childhood obesity is due to ENPP1 SNPs.

TABLE 4

Positive association (p < 0.05) of genotypes and alleles of ENPP1 gene SNPs with obesity. Cases Set 1 = 529 French Caucasian children with BMI higher than the obesity threshold of the 97$^{th}$ percentile. Control Set 1 = 556 non obese and normoglycemic French Caucasian adults. Cases Set 2 = 696 French Caucasian adults with BMI ≧ 40. Control Set 2 = 649 non obese and normoglycemic French Caucasian adults.

| Cohorts | | Genotypes n (frequency) | | | Allele freq. OR (p-val.) | Co-dom. OR (p-val.) | Dominant OR (p-val.) | Recessive OR (p-val.) | HW (p-val.) |
|---|---|---|---|---|---|---|---|---|---|
| | | C > T-768ATG | CC | CT | TT | | | | |
| Set 1 | Obese children | 310 (0.65) | 145 (0.30) | 23 (0.05) | 0.91 (0.42) | 0.91 (0.44) | 0.93 (0.58) | 0.77 (0.37) | 0.25 |
| | Control 1 | 312 (0.63) | 152 (0.31) | 30 (0.06) | | | | | 0.06 |
| Set 2 | Morbidly obese | 385 (0.60) | 225 (0.35) | 30 (0.05) | 1.05 (0.59) | 1.05 (0.59) | 1.07 (0.58) | 1.08 (0.77) | 0.82 |
| | Control 2 | 375 (0.62) | 206 (0.34) | 27 (0.04) | | | | | 0.90 |
| Set 1 + 2 | Obese | 695 (0.62) | 370 (0.33) | 53 (0.05) | 0.99 (0.92) | 0.98 (0.92) | 1.01 (0.93) | 0.92 (0.67) | 0.66 |
| | Control 1 + 2 | 687 (0.62) | 358 (0.33) | 57 (0.05) | | | | | 0.24 |
| | G > T-190ATG | GG | GT | TT | | | | | |
| Set 1 | Obese children | 436 (0.88) | 59 (0.12) | 1 (0.00) | 1.26 (0.24) | 1.25 (0.24) | 1.28 (0.22) | 1.05 (0.97) | 1 |
| | Control 1 | 456 (0.90) | 48 (0.10) | 1 (0.00) | | | | | 1 |
| Set 2 | Morbidly obese | 589 (0.90) | 63 (0.10) | 3 (0.00) | 0.77 (0.12) | 0.79 (0.13) | 0.75 (0.11) | 0.88 (0.87) | 0.41 |
| | Control 2 | 518 (0.87) | 74 (0.12) | 3 (0.01) | | | | | 0.74 |
| Set 1 + 2 | Obese | 1025 (0.89) | 122 (0.11) | 4 (0.00) | 0.95 (0.71) | 0.95 (0.71) | 0.95 (0.70) | 0.95 (0.94) | 0.78 |
| | Control 1 + 2 | 974 (0.89) | 122 (0.11) | 4 (0.00) | | | | | 0.79 |
| | IVS2delG + 8 | G/G | G/delG | delG/delG | | | | | |
| Set 1 | Obese children | 378 (0.88) | 48 (0.11) | 2 (0.01) | 1.34 (0.14) | 1.54 (0.14) | 1.31 (0.20) | 6.55 (0.11) | 0.66 |
| | Control 1 | 495 (0.91) | 50 (0.09) | 0 (0.00) | | | | | 0.62 |
| Set 2 | Morbidly obese | 610 (0.89) | 74 (0.11) | 3 (0.00) | 1.32 (0.12) | 1.34 (0.12) | 1.31 (0.15) | 2.71 (0.37) | 0.49 |
| | Control 2 | 551 (0.91) | 52 (0.09) | 1 (0.00) | | | | | 1 |
| Set 1 + 2 | Obese | 988 (0.89) | 122 (0.11) | 5 (0.00) | 1.33 (0.03) | 1.39 (0.03) | 1.30 (0.05) | 5.29 (0.09) | 0.58 |
| | Control 1 + 2 | 1046 (0.91) | 102 (0.09) | 1 (0.00) | | | | | 0.72 |
| | K121Q | KK | KQ | QQ | | | | | |
| Set 1 | Obese children | 351 (0.67) | 153 (0.29) | 22 (0.04) | 1.45 (0.001) | 1.56 (0.001) | 1.41 (0.01) | 3.63 (0.001) | 0.31 |
| | Control 1 | 405 (0.74) | 136 (0.25) | 7 (0.01) | | | | | 0.28 |
| Set 2 | Morbidly obese | 479 (0.70) | 176 (0.26) | 25 (0.04) | 1.31 (0.01) | 1.41 (0.01) | 1.26 (0.07) | 3.05 (0.004) | 0.09 |
| | Control 2 | 467 (0.75) | 148 (0.24) | 8 (0.01) | | | | | 0.38 |

TABLE 4-continued

Positive association (p < 0.05) of genotypes and alleles of ENPP1 gene SNPs with obesity. Cases Set 1 = 529 French Caucasian children with BMI higher than the obesity threshold of the 97$^{th}$ percentile. Control Set 1 = 556 non obese and normoglycemic French Caucasian adults. Cases Set 2 = 696 French Caucasian adults with BMI ≧ 40. Control Set 2 = 649 non obese and normoglycemic French Caucasian adults.

| Cohorts | | Genotypes n (frequency) | | | Allele freq. OR (p-val.) | Co-dom. OR (p-val.) | Dominant OR (p-val.) | Recessive OR (p-val.) | HW (p-val.) |
|---|---|---|---|---|---|---|---|---|---|
| Set 1 + 2 | Obese | 830 (0.69) | 329 (0.27) | 47 (0.04) | 1.37 (0.00008) | 1.48 (0.00009) | 1.32 (0.002) | 3.29 (0.00003) | 0.06 |
| | Control 1 + 2 | 872 (0.75) | 284 (0.24) | 15 (0.01) | | | | | 0.16 |
| | IVS8T > G + 27 | TT | TG | GG | | | | | |
| Set 1 | Obese children | 377 (0.78) | 105 (0.22) | 2 (0.00) | 1.35 (0.04) | 1.40 (0.03) | 1.39 (0.04) | 2.26 (0.49) | 0.07 |
| | Control 1 | 427 (0.83) | 86 (0.17) | 1 (0.00) | | | | | 0.16 |
| Set 2 | Morbidly obese | 539 (0.81) | 118 (0.18) | 9 (0.01) | 1.26 (0.09) | 1.32 (0.09) | 1.23 (0.15) | 2.83 (0.10) | 0.39 |
| | Control 2 | 508 (0.84) | 94 (0.16) | 3 (0.00) | | | | | 0.79 |
| Set 1 + 2 | Obese | 916 (0.80) | 223 (0.19) | 11 (0.01) | 1.30 (0.009) | 1.35 (0.009) | 1.30 (0.01) | 2.81 (0.06) | 0.64 |
| | Control 1 + 2 | 935 (0.84) | 180 (0.16) | 4 (0.00) | | | | | 0.17 |
| | IVS20delT-11 | T/T | T/delT | delT/delT | | | | | |
| Set 1 | Obese children | 293 (0.56) | 190 (0.36) | 43 (0.08) | 1.10 (0.32) | 1.20 (0.31) | 0.99 (0.92) | 1.96 (0.01) | 0.14 |
| | Control 1 | 307 (0.55) | 224 (0.40) | 23 (0.05) | | | | | 0.03 |
| Set 2 | Morbidly obese | 382 (0.55) | 255 (0.37) | 57 (0.08) | 1.31 (0.002) | 1.32 (0.003) | 1.31 (0.01) | 1.85 (0.007) | 0.12 |
| | Control 2 | 396 (0.62) | 214 (0.33) | 32 (0.05) | | | | | 0.64 |
| Set 1 + 2 | Obese | 675 (0.55) | 445 (0.37) | 100 (0.08) | 1.21 (0.004) | 1.26 (0.004) | 1.15 (0.09) | 1.89 (0.0002) | 0.03 |
| | Control 1 + 2 | 703 (0.59) | 438 (0.36) | 55 (0.05) | | | | | 0.22 |
| | G > C + 121TGA | GG | GC | CC | | | | | |
| Set 1 | Obese children | 443 (0.96) | 17 (0.04) | 1 (0.00) | 0.86 (0.63) | 0.87 (0.64) | 0.85 (0.63) | 0.89 (0.94) | 0.17 |
| | Control 1 | 398 (0.95) | 18 (0.04) | 1 (0.01) | | | | | 0.21 |
| Set 2 | Morbidly obese | 601 (0.94) | 35 (0.06) | 2 (0.00) | 1.62 (0.09) | 1.88 (0.09) | 1.55 (0.13) | 3.98 (0.21) | 0.11 |
| | Control 2 | 478 (0.96) | 19 (0.04) | 0 (0.00) | | | | | 1 |
| Set 1 + 2 | Obese | 1044 (0.95) | 52 (0.05) | 3 (0.00) | 1.24 (0.30) | 1.26 (0.31) | 1.21 (0.37) | 2.52 (0.41) | 0.05 |
| | Control 1 + 2 | 876 (0.96) | 37 (0.04) | 1 (0.00) | | | | | 0.34 |
| | C > T + 164TGA | CC | CT | TT | | | | | |
| Set 1 | Obese children | 436 (0.89) | 55 (0.11) | 1 (0.00) | 0.99 (0.97) | 0.99 (0.97) | 0.99 (0.96) | 1.10 (0.95) | 1 |
| | Control 1 | 478 (0.89) | 61 (0.11) | 1 (0.00) | | | | | 1 |
| Set 2 | Morbidly obese | 607 (0.87) | 83 (0.12) | 6 (0.01) | 1.40 (0.04) | 1.49 (0.05) | 1.35 (0.09) | 5.54 (0.07) | 0.12 |
| | Control 2 | 561 (0.90) | 60 (0.10) | 1 (0.00) | | | | | 1 |
| Set 1 + 2 | Obese | 1043 (0.88) | 138 (0.12) | 7 (0.00) | 1.20 (0.14) | 1.25 (0.14) | 1.17 (0.22) | 3.49 (0.1) | 0.32 |
| | Control 1 + 2 | 1039 (0.90) | 121 (0.10) | 2 (0.00) | | | | | 0.77 |
| | Ins + 828TGA | —/— | —/Ins | Ins/Ins | | | | | |
| Set 1 | Obese children | 454 (0.90) | 50 (0.10) | 2 (0.00) | 1.17 (0.45) | 1.15 (0.45) | 1.19 (0.42) | 1.00 (1) | 0.64 |
| | Control 1 | 456 (0.91) | 42 (0.09) | 2 (0.00) | | | | | 0.28 |
| Set 2 | Morbidly obese | 586 (0.90) | 65 (0.10) | 2 (0.00) | 0.87 (0.40) | 0.87 (0.40) | 0.86 (0.39) | 0.93 (0.94) | 0.7 |
| | Control 2 | 547 (0.88) | 71 (0.12) | 2 (0.00) | | | | | 1 |
| Set 1 + 2 | Obese | 1040 (0.90) | 115 (0.10) | 4 (0.00) | 0.98 (0.89) | 0.98 (0.89) | 0.98 (0.88) | 0.96 (0.96) | 0.56 |
| | Control 1 + 2 | 1003 (0.90) | 113 (0.10) | 4 (0.00) | | | | | 0.56 |
| | A > G + 1044TGA | AA | AG | GG | | | | | |
| Set 1 | Obese children | 260 (0.49) | 213 (0.40) | 56 (0.11) | 1.09 (0.38) | 1.14 (0.38) | 0.99 (0.94) | 1.52 (0.06) | 0.22 |
| | Control 1 | 269 (0.49) | 243 (0.44) | 38 (0.07) | | | | | 0.1 |
| Set 2 | Morbidly obese | 328 (0.50) | 257 (0.39) | 77 (0.11) | 1.36 (0.0004) | 1.36 (0.0006) | 1.36 (0.006) | 1.97 (0.0008) | 0.02 |
| | Control 2 | 369 (0.57) | 233 (0.36) | 44 (0.07) | | | | | 0.40 |

TABLE 4-continued

Positive association (p < 0.05) of genotypes and alleles of ENPP1 gene SNPs
with obesity. Cases Set 1 = 529 French Caucasian children with BMI higher than the
obesity threshold of the 97th percentile. Control Set 1 = 556 non obese and
normoglycemic French Caucasian adults. Cases Set 2 = 696 French Caucasian adults
with BMI ≧ 40. Control Set 2 = 649 non obese and normoglycemic French Caucasian adults.

| Cohorts | | Genotypes n (frequency) | | | Allele freq. OR (p-val.) | Co-dom. OR (p-val.) | Dominant OR (p-val.) | Recessive OR (p-val.) | HW (p-val.) |
|---|---|---|---|---|---|---|---|---|---|
| Set 1 + 2 | Obese | 588 (0.49) | 470 (0.40) | 133 (0.11) | 1.22 (0.002) | 1.26 (0.002) | 1.17 (0.05) | 1.76 (0.0002) | 0.01 |
| | Control 1 + 2 | 638 (0.53) | 476 (0.40) | | | | | | 0.66 |
| | T > G + 5954TGA | TT | TG | GG | | | | | |
| Set 1 | Obese children | 366 (0.77) | 100 (0.21) | 10 (0.02) | 1.43 (0.01) | 1.47 (0.02) | 1.41 (0.03) | 2.9 (0.06) | 0.30 |
| | Control 1 | 426 (0.82) | 87 (0.17) | 4 (0.01) | | | | | 1 |
| Set 2 | Morbidly obese | 532 (0.79) | 126 (0.19) | 11 (0.02) | 1.24 (0.09) | 1.26 (0.10) | 1.23 (0.14) | 1.85 (0.22) | 0.24 |
| | Control 2 | 536 (0.83) | 106 (0.16) | 6 (0.01) | | | | | 0.81 |
| Set 1 + 2 | Obese | 898 (0.78) | 226 (0.20) | 21 (0.02) | 1.32 (0.004) | 1.34 (0.005) | 1.30 (0.01) | 2.25 (0.03) | 0.15 |
| | Control 1 + 2 | 962 (0.83) | 193 (0.16) | 10 (0.01) | | | | | 0.86 |

Example 4

Characterization of a Three Allele Risk Haplotype Strongly Associated with Severe Forms of Obesity A two SNP analysis between the K121Q polymorphism and the 6 other obesity-associated SNPs was used to assess whether these SNPs had an independent effect on the risk of obesity. A likelihood ratio test showed that only IVS20delT–11 and G+1044TGA SNPs significantly modulate the effect of K121Q (p=0.03 and p=0.04 respectively). It is worth pointing out that for these two SNPs, the model with the best fit was also a recessive one. This may account for the small observed deviation from Hardy-Weinberg Equilibrium (HWE) for these SNPs as genotyping errors have been ruled out by resequencing (data not shown). Such a deviation can be expected in affected "extreme" individuals when the genetic model is not strictly additive[21].

In order to estimate the potential cumulative effect of combinations of the three SNPs on the risk of obesity, haplotype analysis was performed using the K121Q, IVS20 delT–11 and A>G +1044 TGA SNP data from the whole set of 2,430 French Caucasian subjects. Eight haplotypes were predicted, five of them having a MAF>5%. As shown in Table 5, the three allele wild-type haplotype (K121Q/IVS20 delT–11/A>G +1044 TGA, KTA), was less frequent in obese subjects than in controls (60.3% vs 64.0%, p=0.002). In contrast, the three allele risk haplotype (K121Q/IVS20 delT–11/A>G +1044 TGA, QdelTG), was strongly associated with severe forms of obesity (11.2% vs 7.5%, OR=1.58, p=0.00001, empirical p-value<0.0001 for $10^5$ simulations). Interestingly, the risk haplotype effect was of similar magnitude in both morbidly obese adults and childhood obesity (10.8% vs 7.9%, OR=1.50, p=0.006, and 11.7% vs 7.1%, OR=1.69, p=0.0006, respectively). The association was also supported by TDT analysis in the 184 families (Chi2=5.68, p=0.01, Table 5).

TABLE 5

Haplotype analysis of 1225 morbidly obese/obese children and 1205 control
subjects. Haplotypes comprising three polymorphisms (K121Q, IVS20 delT-11,
A > G + F1044 TGA) are shown. TDT was performed for each haplotype in 97 pedigrees
with childhood obesity and in 87 pedigrees with adult obesity

| Haplotypes | | | Case/control Test | | | | TDT in 184 obesity pedigrees | |
|---|---|---|---|---|---|---|---|---|
| K121Q | IVS20 delT-11 | A > G + 1044TGA | Non obese | Obese | Chi-square | p-value | Chi-square | p-value |
| K | T | A | 64.0 | 60.3 | 8.99 | 0.003 | 2.7 | 0.1 |
| | | G | 7.0 | 7.6 | 0.51 | 0.47 | 0.09 | 0.75 |
| | DelT | A | 3.5 | 2.7 | 1.26 | 0.26 | 0 | 1 |
| | | G | 11.7 | 11.9 | 0.18 | 0.67 | 0.73 | 0.39 |
| Q | T | A | 5.5 | 4.8 | 0.15 | 0.70 | 2.30 | 0.13 |
| | | G | 0.6 | 0.6 | 0.19 | 0.66 | 0 | 1 |
| | DelT | A | 0.2 | 0.9 | 5.23 | 0.02 | 0.20 | 0.65 |
| | | G | 7.5 | 11.2 | 18.78 | 0.00001 | 5.68 | 0.01 |

TDT analysis in 458 french Caucasian control trios (2 parents and one lean child) didn't show an excess of transmission of the risk haplotype (Chi2=0.53, p=0.46, data not shown) and excluded a transmission ratio distortion of the risk haplotype in unaffected children[22]. Finally, we evaluated the effect of the haplotypes in an additional set of 717 adult subjects with a less severe form of obesity (BMI between 30 and 40 kg/m$^2$), compared against the 649 non-obese normoglycemic control subjects used previously. Again, the risk haplotype was associated with obesity (10.3% vs 7.9%, OR=1.37, p=0.02).

Several approaches were used to test the impact of the ENPP1 risk haplotype on the linkage with childhood obesity observed in the genome scan. We first detected a higher frequency of the risk haplotype in individuals from "6q-evidence" families (16.2% vs 7.1%, OR=2.37, p=0.004) compared to other families (12.2% vs 7.1%, OR=1.65, p=0.16). The affected sib-pairs sharing the obesity-associated risk haplotype (15 from a total of 135), when analyzed separately, gave a maximal multipoint MLS LOD score of 3.49 at the position of the initial maximum linkage (marker D6S287). Conversely, after removing these 15 affected sib-pairs, the multipoint MLS LOD score dropped from 4.06 to 1.6 at marker D6S287, and a new maximal MLS LOD score of 2.63 appeared 16-Mb centromeric to the original peak of linkage, at the marker D6S301. To evaluate the significance of these variations, the Genotype IBD Sharing Test (GIST) was used[23]. This test suggested a trend to for a possible effect of the haplotype under an additive model (p=0.07) which became significant for a recessive model (p=0.03), but this was based upon only three affected sib-pairs sharing two copies of the haplotype. Altogether, these data suggest some contribution of the ENPP1 obesity risk haplotype to the observed linkage with childhood obesity on chromosome 6q, though the GIST result demonstrates that it is relatively modest.

According to these data, at least three ENPP1 SNPs are involved in the association with obesity. The Q121 variant is believed to inhibit insulin signalling[11] more effectively than the wild-type version, but the functional effects of the risk haplotype are unknown.

Example 5

Highly Significant Increase of ENPP1 Levels Associated with K121Q, IVS20delT-11 and G+1044TGA Alleles The ENPP1 protein has a proteolytic cleavage site, is cleaved at the surface of cells, and is known to be present in the circulation[24]. Thus, the protein serum level represents a good estimation of its tissue expression[24]. Serum ENPP1 protein levels measured in 279 children encompassing a wide weight range showed a positive correlation with the Z score of BMI (Pearson correlation coefficient=0.1, p=0.05, FIG. 3). Eighty-nine lean children were then selected (mean BMI, 18.4±2.5 kg/m$^2$; mean age, 13.3±2.6y; n=50/39 girl/boy), to fix the confounder BMI, and analyzed for the effect of the three SNPs on ENPP1 levels. The presence of at least one copy of Q121, IVS20delT-11 and G+1044TGA alleles was associated with a highly significant increase of ENPP1 levels (28.6 ng/ml vs 24.1 ng/ml, p=0.008) (FIG. 4), suggesting that the obesity-associated haplotype not only impairs insulin binding but also enhances ENPP1 levels of expression.

The inventors then assessed the contribution of the risk haplotype on the variation of obesity-related phenotypes in 474 obese children where data were available. Obese children with the obesity-associated risk haplotype showed a 0.17 mmol/l increase in fasting glycemia (p=0.002) with a higher prevalence of glucose intolerance/T2D (OR=3.43, p=0.02). Parents carrying the risk haplotype had a 2.35 fold increased risk to develop T2D (p=0.005). Moreover, the risk was higher in the subset of obese parents (OR=3.26, p=0.0005) whereas no increase in the risk of T2D was observed in the non obese parents carrying the risk haplotype (OR=0.86, p=0.9). To confirm the association of the ENPP1 SNPs with T2D, an additional non overlapping cohort of 752 unrelated T2D French Caucasian subjects with familial history of the disease was compared to the previously used 556 middle aged non obese normoglycemic subjects (average age: 55±6 years). A significant excess of the risk haplotype was identified in the T2D group (10.7% vs 7.1%, OR=1.44, p=0.005), further supporting a potential effect of ENPP1 SNPs on glucose homeostasis in French Caucasians. This finding was then replicated using 1261 unrelated Austrian subjects consisting of 503 T2D subjects and 758 non obese normoglycemic subjects (9.8% vs 6.3%, OR=1.68, p=0.001). Because of potential differences in allele frequency and effect size between the French and Austrian cohorts, the Mantel Haenszel adjusted odds ratio, under a fixed effects model, was used to evaluate the risk of T2D in the pooled cohorts. The pooled data, with 2569 individuals of European origin, strengthened the association of the risk haplotype with T2D (10.4% vs 6.6%, combined OR=1.56, p=0.00002). In summary, these findings indicate that both obesity and T2D, especially in obese subjects, are associated with ENPP1 genetic variability and specifically, a single three allele risk haplotype. This provides genetic evidence for the recently described link between obesity in childhood and the high risk for T2D in the teens or early adulthood[25], providing the first common molecular mechanism for this deleterious association.

The tissue distribution of ENPP1 transcripts was examined next. RT-PCR was performed on cDNAs from a wide range of human tissues including brain, muscle, liver, adipocyte (subcutaneous and omental), and purified pancreatic islet beta-cells. Taking into account that five ENPP1 isoforms are known, (http://www.ncbi.nih.gov/IEB/Research/Acembly/av.cgi?db=human&1=ENPP1, we designed primers to amplify the region between exons 7 and 12, which is common to at least 3 transcripts, and found ubiquitous expression (see FIG. 5). Primers were then designed that were specific to the long mRNA isoform, characterized by a larger 3'UTR with 1170 bases downstream of the TGA stop codon and including the obesity-associated SNP A>G +1044 TGA. The long form was found to be only expressed in pancreatic β-cells, adipocytes and liver, three key tissues for glucose homeostasis (see supplementary FIG. 1).

This study provides the first evidence for a primary role of variants of ENPP1 gene variants in the development of both childhood and adult morbid and less severe forms of obesity and strong evidence for an association with T2D that could be increased by the concurrent presence of obesity. This extensive analysis of the whole ENPP1 locus in the context of metabolic diseases revealed that this effect is mainly the result of a newly described three allele risk haplotype that was a more potent predictor than individual SNPs in all the studied populations.

The likely contribution of the obesity-associated ENPP1 risk haplotype to our observed linkage with childhood obesity on 6q was assessed by several methods including the recently described Genotype IBD Sharing Test (GIST) procedure[23]. A significantly higher frequency of the risk haplotype was observed in affected individuals from "6q-evidence" families together with a significant correlation between the haplotype specific index and the NPL score in the GIS test. In this regard, Jenkinson et al. recently presented preliminary data which support a contribution of ENPP1 SNPs[26] to the linkage for insulin fasting levels observed in Mexican-Americans[3]. As we also found evidence for association between ENPP1 SNPs and T2D, this gene may also contribute to the linkage peaks with T2D and related traits found in other populations[3-8]. However, in spite of the strong association of the three allele haplotype with severe forms of obesity in the French Caucasian population (OR=1.58, p=0.00001) and the evidence for its contribution to the 6q linkage signal, we only found a moderate excess of transmission of this haplotype to affected offspring as measured by the TDT (p=0.01). This suggests that the risk haplotype is necessary for the linkage, thus showing a higher frequency in "linked" individuals, but not sufficient to fully explain it. That implies other contributing sequences in the 6q linked region.

It is plausible that additional SNPs in the non-coding regions of the ENPP1 locus account for a part of the observed linkage. For instance, the SNP T>G +5954 TGA, included in a highly conserved region across *Fugu rubripes*, rat and human genomes, showed association with severe forms of obesity. Using Genomatix (http://www.genomatix.de/) we found that the polymorphism was part of a sequence (aaaaaat-tcTT(>G)ATgacaccta) recognized by the Insulin Promoter Factor IPF1[27]. The substitution from T to G predicts loss of binding IPF1, suggesting that this SNP could be functional. Alternatively, more than one gene may explain the linkage with obesity and T2D on 6q. Such a situation has been already described on chromosome 16 for Crohn's disease[28,29]. In this regard, the 16 Mb centromeric linkage peak shift when ENPP1 risk obesity-associated haplotype carriers are discarded coincides with the location of Single-minded 1 (SIM1), another obesity candidate gene[30,31].

The putative functionality of the three obesity-associated SNPs was primarily assessed by statistical means, including a likelihood ratio test of haplotype effects, using THESIAS software[32]. Among these SNPs, the ENPP1 K121Q exon 4 missense mutation has been previously associated with insulin resistance in rather small size samples from Sicily, Scandinavia and India[14-17], and with T2D in Dominicans[18], but has never been confirmed in large scale studies. The present study involves a total of 6,147 subjects, all of European origin, and confirms the T2D findings and expands them to include obesity. The other two strongly obesity-associated SNPs are located in the exon 21 boundary (IVS20delT-11) and in the 3'UTR (A>G +1044 TGA). Interestingly, the latter belongs to an isoform that is specifically expressed in three highly insulin-responsive human tissues (pancreatic islet β-cell, adipocyte and liver) which are thought to play a major role in T2D pathophysiology. Highlighting the importance of ENPP1 action in the liver, mice given an adenovirus expression construct overexpressing this gene in hepatocytes show insulin resistance and glucose intolerance[10]. Although the exonic 121Q amino acid substitution was proposed to directly inhibit insulin receptor by a non enzymatic mechanism[11], the other non-coding SNPs may have their effect by modifying gene expression, protein production or splicing, both increasing the protein's putative deleterious effect on insulin signaling. This hypothesis is favoured by the increased serum protein levels in children carrying the ENPP1 obesity risk haplotype and also by the rise of ENPP1 levels with adiposity. Whether this effect is haplotype specific or is unrelated to genetic phase needs to be ascertained in larger family cohorts.

Our study has demonstrated that ENPP1 mRNA is present in cellular types responsive to insulin, and higher protein expression may mimic to a certain extent the effects of insulin receptor inactivation in the brain where insulin has potent anorectic actions[33], or in the skeletal muscle, both leading to an increased fat mass[34,35]. In addition, insulin receptor knockout mice in liver[36] or in β-cell[37] are glucose intolerant. Conversely, Um et al. recently demonstrated in S6K1-deficient mice that protection against age and diet-induced obesity was associated with an enhanced insulin sensitivity[38]. In the current study obese children carrying the ENPP1 risk haplotype have a strong family history of T2D and are more often intolerant to glucose load. This suggests that the exaggerated insulin resistance conferred by inherited increased ENPP1 expression in the liver, muscle and adipose tissue (and possibly in the brain and the pancreatic (β-cell), in the context of a very strong Westernized obesogenic environment, may modify nutrition partitioning and contribute to excessive fat accumulation. In this regard Barroso et al. recently showed that the ENPP1 Q121 allele was associated with increased BMI in the UK general population[39]. The data presented here support the view of a causative effect of primary insulin resistance on childhood obesity which can be viewed as a "pre-diabetic" state[25]. According to this hypothesis, insulin resistance-induced fasting hyperinsulinemia was shown to be a strong predictor for the subsequent development of obesity in children of various ethnic groups[40,41].

In conclusion, this study strongly supports a genetic link between ENPP1 gene variants and chromosome 6q-linked childhood polygenic obesity and also with adult obesity and T2D. Our data provide an insight into the molecular basis for the physiologic association between insulin resistance and obesity, and therefore present a new perspective for prevention, and treatment of these conditions.

REFERENCES

1. Meyre, D. et al. A genome-wide scan for childhood obesity-associated traits in French families shows significant linkage on chromosome 6q22.31-q23.2. Diabetes 53, 803-11 (2004).
2. Atwood, L. D. et al. Genomewide Linkage Analysis of Body Mass Index across 28 Years of the Framingham Heart Study. Am J Hum. Genet. 71, 1044-50 (2002).
3. Duggirala, R. et al. A major locus for fasting insulin concentrations and insulin resistance on chromosome 6q with strong pleiotropic effects on obesity-related phenotypes in nondiabetic Mexican Americans. Am. J. Hum. Genet. 68, 1149-64 (2001).
4. Abney, M., Ober, C. & McPeek, M. S. Quantitative-trait homozygosity and association mapping and empirical genomewide significance in large, complex pedigrees: fasting serum-insulin level in the Hutterites. Am. J. Hum. Genet. 70, 920-34 (2002).
5. Gelder Ehm, M. G. et al. Genomewide search for type 2 diabetes susceptibility genes in four American populations. Am J Hum. Genet. 66, 1871-81 (2000).
6. Ghosh, S. et al. The Finland-United States investigation of non-insulin-dependent diabetes mellitus genetics (FUSION) study. I. An autosomal genome scan for genes that predispose to type 2 diabetes. Am. J. Hum. Genet. 67, 1174-85 (2000).
7. Demenais, F. et al. A meta-analysis of four European genome screens (GIFT Consortium) shows evidence for a novel region on chromosome 17p11.2-q22 linked to type 2 diabetes Hum Mol Genet. 12, 1865-73 (2003).
8. Xiang, K. et al. Genome-Wide Search for Type 2 Diabetes/Impaired Glucose Homeostasis Susceptibility Genes in the Chinese: Significant Linkage to Chromosome 6q21-q23 and Chromosome 1q21-q24. Diabetes 53, 228-34 (2004).
9. Maddux, B. A. et al. Membrane glycoprotein PC-1 and insulin resistance in non-insulin-dependent diabetes mellitus. Nature 373, 448-51 (1995).
10. Dong, H. et al. Increased Hepatic Levels of the Insulin Receptor Inhibitor, PC-1/NPP1, Induce Insulin Resistance and Glucose Intolerance. Diabetes 54, 367-72 (2005).

11. Costanzo, B. V. et al. The Q allele variant (GLN121) of membrane glycoprotein PC-1 interacts with the insulin receptor and inhibits insulin signaling more effectively than the common K allele variant (LYS121). Diabetes 50, 831-6 (2001).
12. Rolland-Cachera, M. F. et al. Body Mass Index variations: centiles from birth to 87 years. Eur J Clin Nutr 45, 13-21 (1991).
13. Maddux, B. A. & Goldfine, I. D. Membrane glycoprotein PC-1 inhibition of insulin receptor function occurs via direct interaction with the receptor alpha-subunit. Diabetes 49, 13-19 (2000).
14. Pizzuti, A. et al. A polymorphism (K121Q) of the human glycoprotein PC-1 gene coding region is strongly associated with insulin resistance. Diabetes 48, 1881-4 (1999).
15. Gu, H. F. et al. Association between the human glycoprotein PC-1 gene and elevated glucose and insulin levels in a paired-sibling analysis. Diabetes 49, 1601-3 (2000).
16. Kubaszek, A., Pihlajamaki, J., Karhapaa, P., Vauhkonen, I. & Laakso, M. The K121Q polymorphism of the PC-1 gene is associated with insulin resistance but not with dyslipidemia. Diabetes Care 26, 464-7 (2003).
17. Abate, N. et al. Genetic polymorphism PC-1 K121Q and ethnic susceptibility to insulin resistance. J Clin Endocrinol Metab 88, 5927-34 (2003).
18. Hamaguchi, K. et al. The PC-1 Q121 allele is exceptionally prevalent in the Dominican Republic and is associated with type 2 diabetes. J Clin Endocrinol Metab 89, 1359-64 (2004).
19. Frittitta, L. et al. A cluster of three single nucleotide polymorphisms in the 3'-untranslated region of human glycoprotein PC-1 gene stabilizes PC-1 mRNA and is associated with increased PC-1 protein content and insulin resistance-related abnormalities. Diabetes 50, 1952-5 (2001).
20. Hager, J. et al. A genome-wide scan for human obesity genes reveals a major susceptibility locus on chromosome 10. Nat Genet. 20, 304-8 (1998).
21. Deng, H. W., Chen, W. M. & Recker, R. R. QTL fine mapping by measuring and testing for Hardy-Weinberg and linkage disequilibrium at a series of linked marker loci in extreme samples of populations. Am J Hum Genet. 66, 1027-45 (2000).
22. Eaves, I. A. et al. Transmission ratio distortion at the INS-IGF2 VNTR. Nat Genet. 22, 324-5 (1999).
23. Li, C., Scott, L. J. & Boehnke, M. Assessing whether an allele can account in part for a linkage signal: the Genotype-IBD Sharing Test (GIST). Am J Hum Genet. 74, 418-31 (2004).
24. Rutsch, F. et al. PC-1 nucleoside triphosphate pyrophosphohydrolase deficiency in idiopathic infantile arterial calcification. Am J Pathol 158, 543-54 (2001).
25. Weill, J., Vanderbecken, S. & Froguel, P. Understanding the rising incidence of type 2 diabetes in adolescence. Arch Dis Child 89, 502-4 (2004).
26. Jenkinson, C. P. et al. Comprehensive analysis of snps in ENPP1: association with diabesity. ASHG abstract (2004).
27. Ohlsson, H., Karlsson, K. & Edlund, T. IPF1, a homeodomain-containing transactivator of the insulin gene. Embo J 12, 4251-9 (1993).
28. Hugot, J. P. et al. Association of NOD2 leucine-rich repeat variants with susceptibility to Crohn's disease. Nature 411, 599-603 (2001).
29. Hampe, J. et al. Evidence for a NOD2-independent susceptibility locus for inflammatory bowel disease on chromosome 16p. Proc Natl Acad Sci USA 99, 321-6 (2002).
30. Holder, J. L., Jr., Butte, N. F. & Zinn, A. R. Profound obesity associated with a balanced translocation that disrupts the SIM1 gene Hum Mol Genet. 9, 101-8. (2000).
31. Michaud, J. L. et al. Sim1 haploinsufficiency causes hyperphagia, obesity and reduction of the paraventricular nucleus of the hypothalamus Hum Mol Genet. 10, 1465-73 (2001).
32. Tregouet, D. A., Escolano, S., Tiret, L., Mallet, A. & Golmard, J. L. A new algorithm for haplotype-based association analysis: the Stochastic-EM algorithm. Ann Hum Genet. 68, 165-77 (2004).
33. Schwartz, M. W. Progress in the search for neuronal mechanisms coupling type 2 diabetes to obesity. J Clin Invest 108, 963-4 (2001).
34. Bruning, J. C. et al. Role of brain insulin receptor in control of body weight and reproduction. Science 289, 2122-5 (2000).
35. Kim, J. K. et al. Redistribution of substrates to adipose tissue promotes obesity in mice with selective insulin resistance in muscle. J Clin Invest 105, 1791-7 (2000).
36. Michael, M. D. et al. Loss of insulin signaling in hepatocytes leads to severe insulin resistance and progressive hepatic dysfunction. Mol Cell 6, 87-97 (2000).
37. Kulkarni, R. N. et al. Tissue-specific knockout of the insulin receptor in pancreatic beta cells creates an insulin secretory defect similar to that in type 2 diabetes. Cell 96, 329-39 (1999).
38. Um, S. H. et al. Absence of S6K1 protects against age- and diet-induced obesity while enhancing insulin sensitivity. Nature 431, 200-205 (2004).
39. Barroso, I. et al. Candidate Gene Association Study in Type 2 Diabetes Indicates a Role for Genes Involved in beta-Cell Function as Well as Insulin Action. PLoS Biol 1, E20 (2003).
40. Odeleye, O. E., de Courten, M., Pettitt, D. J. & Ravussin, E. Fasting hyperinsulinemia is a predictor of increased body weight gain and obesity in Pima Indian children. Diabetes 46, 1341-5 (1997).
41. Johnson, M. S., Figueroa-Colon, R., Huang, T. T., Dwyer, J. H. & Goran, M. I. Longitudinal changes in body fat in African American and Caucasian children: influence of fasting insulin and insulin sensitivity. J Clin Endocrinol Metab 86, 3182-7 (2001).
42. Poskitt, E. M. Defining childhood obesity: the relative body mass index (BMI). European Childhood Obesity group. Acta Paediatr 84, 961-3 (1995). 43. Hercberg, S. et al. A primary prevention trial using nutritional doses of antioxidant vitamins and minerals in cardiovascular diseases and cancers in a general population: the SU.VI.MAX study-design, methods, and participant characteristics. SUpplementation en VItamines et Mineraux AntioXydants. Control Clin Trials 19, 336-51 (1998).
44. Lafay, L. et al. Determinants and nature of dietary underreporting in a free-living population: the Fleurbaix Laventie Ville Sante (FLVS) Study. Int J Obes Relat Metab Disord 21, 567-73 (1997).
45. Oberkofler, H. et al. Complex haplotypes of the PGC-1alpha gene are associated with carbohydrate metabolism and type 2 diabetes. Diabetes 53, 1385-93 (2004).
46. Cole, T. J. The LMS method for constructing normalized growth standards. Eur J Clin Nutr 44, 45-60 (1990).
47. Seltzer, H. S., Allen, E. W., Herron, A. L., Jr. & Brennan, M. T. Insulin secretion in response to glycemic stimulus: relation of delayed initial release to carbohydrate intolerance in mild diabetes mellitus. J Clin Invest 46, 323-35 (1967).

48. Risch, N. Linkage strategies for genetically complex traits. I. Multilocus models. Am J Hum Genet. 46, 222-228 (1990).
49. Kruglyak, L. & Lander, E. S. Complete multipoint sib-pair analysis of qualitative and quantitative traits. Am J Hum Genet. 57, 439-54 (1995).
50. Sham, P. C. & Curtis, D. Monte Carlo tests for associations between disease and alleles at highly polymorphic loci. Ann Hum Genet. 59 (Pt 1), 97-105 (1995).
51. Dudbridge, F., Koeleman, B. P., Todd, J. A. & Clayton, D. G. Unbiased application of the transmission/disequilibrium test to multilocus haplotypes. Am J Hum Genet. 66, 2009-12 (2000).
52. Lukowiak, B. et al. Identification and purification of functional human beta-cells by a new specific zinc-fluorescent probe. J Histochem Cytochem 49, 519-28 (2001).

The invention claimed is:

1. Method for determining if a human subject is at increased risk to develop obesity or type 2 diabetes, said method comprising the steps of:
   a) obtaining a biological sample from said human subject, wherein said biological sample contains genomic DNA or RNA;
   b) performing a nucleic acid detection assay to detect in the biological sample the presence or absence of a three allele risk haplotype on at least one gene allele or RNA sequence encoding the protein ENPP1, wherein said three allele risk haplotype comprises the three following SNPs:
   K121Q,
   IVS20 delT−11, and
   a A>G +1044 TGA SNP localized in the 3'UTR domain sequence; and
   c) determining whether or not the human subject is at increased risk to develop obesity or type 2 diabetes by observing if said DNA or RNA, or fragments thereof, contains said three allele risk haplotype, wherein the presence of said three allele risk haplotype indicates that said human subject is at increased risk to develop obesity or type 2 diabetes.

2. Method according to claim 1, wherein said nucleic acid detection assay is polymerase chain reaction (PCR), and wherein said PCR is carried out on the biological sample by amplification of the genomic DNA or RNA sequence, or fragments thereof, susceptible to contain one or more of said SNPs.

3. Method according to claim 1, wherein the human subject is determined to be at high risk of developing obesity or type 2 diabetes if the subject is determined to be homozygous for said three allele risk haplotype.

4. Method according to claim 2, wherein the step of PCR is carried out from genomic DNA or RNA, or fragments thereof, or wherein the step of PCR is carried out from cDNA, or fragments thereof, wherein said cDNA, or fragments thereof, are generated after a step of reverse transcription, and wherein the step of PCR is carried out by using the following sets of primers:

a) 5'-TCATACTCAGGAAGACAGCAA-3' (forward primer SEQ ID No. 2) and 5'-CAATAGCCATGACTC-CTAA-3' (reverse primer SEQ ID No. 3) for "K121Q" SNP;
b) 5'-AGCATTTTTACACTTTAGTT-3'(forward primer SEQ ID No. 4) and 5'-ATAATGTATGGTAGGATTT-3' (reverse primer SEQ ID No. 5) for IVS20 delT −11 SNP; and
c) 5'-ATATTCCTATCCTGCTCACT-3' (forward primer SEQ ID No. 6) and 5'-TGCAGCTGGCCCTTAG-GCCG-3' (reverse primer SEQ ID No. 7) for A>G +1044 TGA SNP.

5. Method according to claim 1, wherein said biological sample is a sample of liver, adipocytes or pancreatic beta-cells when the presence of said three allele risk haplotype is determined on RNA sequence or fragments thereof.

6. Method according to claim 1, further comprising the steps of:
   i) obtaining a serum or plasma sample from said human subject; and
   ii) determining the concentration of the ENPP1 protein in said serum or said plasma sample;
   wherein the presence of a significantly higher concentration of ENPP1 protein in said serum or said plasma sample as compared to a normal control sample further indicates that said human subject is at increased risk to develop obesity or type 2 diabetes.

7. Method according to claim 6, wherein said significantly higher concentration of ENPP1 protein in said serum or said plasma sample is at least more than 10% or more than 15% of the normal serum or plasma concentration.

8. Method according to claim 6, wherein said determining the concentration of the ENPP1 protein comprises the use of antibodies capable of specifically recognizing the ENPP1 protein.

9. Method according to claim 8, wherein said antibodies are brought into contact with said serum or said plasma under conditions allowing the formation of a specific immunological complex between the ENPP1 protein and said antibody, wherein the immunological complexes formed are quantified.

* * * * *

UNITED STATES PATENT AND TRADEMARK OFFICE
CERTIFICATE OF CORRECTION

| | |
|---|---|
| PATENT NO. | : 8,017,324 B1 |
| APPLICATION NO. | : 11/917586 |
| DATED | : September 13, 2011 |
| INVENTOR(S) | : Froguel et al. |

It is certified that error appears in the above-identified patent and that said Letters Patent is hereby corrected as shown below:

On the face of the patent, (73) Assignees:

"Universite de Droit de la La Sante de Lille 2" should be:

--Universite de Droit et de la Sante de Lille 2--.

Signed and Sealed this
Third Day of January, 2012

David J. Kappos
*Director of the United States Patent and Trademark Office*

SEQUENCE LISTING

<160> NUMBER OF SEQ ID NOS: 15

<210> SEQ ID NO 1
<211> LENGTH: 832
<212> TYPE: DNA
<213> ORGANISM: Homo sapiens
<220> FEATURE:
<223> OTHER INFORMATION: Fragment of the ENPP1 gene

<400> SEQUENCE: 1

```
aaaaattagc caggcgtggt gggtcacacc tgtaatccca gcactttgag ggggctgcag      60
cggatggatc acctgaggtc aggagctcaa gaccagcctt gccaacatgg tgaaacccca     120
tctctaccaa aaacacaaaa attagccagg cgtggtggca gatgcctgta gtcccagcta     180
ctcgggaagc tgaggcagga aatcgcttg aacctggggg gcagagttgc ggtgagccga      240
gattgcgccg ctgccctcta gtctgggtga cagagtgaga ctccatctta aaaaaataat     300
aataataaat aaataaataa ataaataaat atttaaaatt gtgtagataa aatcattcta     360
aacattattt catattagca tagcagaatc tgaaaatatt tgcataaata tgacaattaa     420
tatctttaat attgtaaagc atttttacac tttagttaga aaaaagatg aatatactag      480
taggaaaata gggaaggaca tgagctgaca gctagagctt cataatttta tgatgtagtt     540
caccctttaaa tattaataaa gcaatttct tctctgtgcc tgatatctga gagttcttct     600
cattttcgtt cttcaggaca gtttctctac ggaagacttc tccaactgtc tgtaccagga     660
ctttagaatt cctcttagtc ctgtccataa atgttcattt tataaaaata acaccaaagt     720
gagttacggg ttcctctccc caccacgtaa gttttttcct ctcctgacct tcccttttct     780
ccttttttgtt ttctttcttg tttataaatc ctaccataca ttataggggta at           832
```

<210> SEQ ID NO 2
<211> LENGTH: 21
<212> TYPE: DNA
<213> ORGANISM: Artificial Sequence
<220> FEATURE:
<223> OTHER INFORMATION: Primer for the human protein ENPP1

<400> SEQUENCE: 2

```
tcatactcag gaagacagca a                                                 21
```

<210> SEQ ID NO 3
<211> LENGTH: 19
<212> TYPE: DNA
<213> ORGANISM: Artificial Sequence
<220> FEATURE:
<223> OTHER INFORMATION: Primer for the human protein ENPP1

<400> SEQUENCE: 3

```
caatagccat gactcctaa                                                    19
```

<210> SEQ ID NO 4

```
<211> LENGTH: 20
<212> TYPE: DNA
<213> ORGANISM: Artificial Sequence
<220> FEATURE:
<223> OTHER INFORMATION: Primer for the human protein ENPP1

<400> SEQUENCE: 4
agcattttta cactttagtt                                              20

<210> SEQ ID NO 5
<211> LENGTH: 19
<212> TYPE: DNA
<213> ORGANISM: Artificial Sequence
<220> FEATURE:
<223> OTHER INFORMATION: Primer for the human protein ENPP1

<400> SEQUENCE: 5
ataatgtatg gtaggattt                                               19

<210> SEQ ID NO 6
<211> LENGTH: 20
<212> TYPE: DNA
<213> ORGANISM: Artificial Sequence
<220> FEATURE:
<223> OTHER INFORMATION: Primer for the human protein ENPP1

<400> SEQUENCE: 6
atattcctat cctgctcact                                              20

<210> SEQ ID NO 7
<211> LENGTH: 20
<212> TYPE: DNA
<213> ORGANISM: Artificial Sequence
<220> FEATURE:
<223> OTHER INFORMATION: Primer for the human protein ENPP1

<400> SEQUENCE: 7
tgcagctggc ccttaggccg                                              20

<210> SEQ ID NO 8
<211> LENGTH: 27
<212> TYPE: DNA
<213> ORGANISM: Artificial Sequence
<220> FEATURE:
<223> OTHER INFORMATION: Primer for the human protein ENPP1

<400> SEQUENCE: 8
ctttccccaa tcactacagc attgtca                                      27

<210> SEQ ID NO 9
<211> LENGTH: 27
<212> TYPE: DNA
<213> ORGANISM: Artificial Sequence
<220> FEATURE:
<223> OTHER INFORMATION: Primer for the human protein ENPP1

<400> SEQUENCE: 9
tttcagacca tccatcagca taccaac                                      27

<210> SEQ ID NO 10
<211> LENGTH: 25
<212> TYPE: DNA
<213> ORGANISM: Artificial Sequence
<220> FEATURE:
<223> OTHER INFORMATION: Primer for the human protein ENPP1

<400> SEQUENCE: 10
```
gtcctgtgtt tgactttgat tatga                                                25

<210> SEQ ID NO 11
<211> LENGTH: 25
<212> TYPE: DNA
<213> ORGANISM: Artificial Sequence
<220> FEATURE:
<223> OTHER INFORMATION: Primer for the human protein ENPP1

<400> SEQUENCE: 11
cccttaggcc gttgaagaat ggtca                                                25

<210> SEQ ID NO 12
<211> LENGTH: 32
<212> TYPE: DNA
<213> ORGANISM: Artificial Sequence
<220> FEATURE:
<223> OTHER INFORMATION: Primer for the human protein beta-actin

<400> SEQUENCE: 12
cgtcatactc ctgcttgctg atccacatct gc                                        32

<210> SEQ ID NO 13
<211> LENGTH: 32
<212> TYPE: DNA
<213> ORGANISM: Artificial Sequence
<220> FEATURE:
<223> OTHER INFORMATION: Primer for the human protein beta-actin

<400> SEQUENCE: 13
atctggcacc acaccttcta caatgagctg cg                                        32

<210> SEQ ID NO 14
<211> LENGTH: 873
<212> TYPE: PRT
<213> ORGANISM: Homo sapiens
<220> FEATURE:
<223> OTHER INFORMATION: Human ENPP1 protein

<400> SEQUENCE: 14

Met Asp Val Gly Glu Glu Pro Leu Glu Lys Ala Ala Arg Ala Arg Thr
 1               5                  10                  15

Ala Lys Asp Pro Asn Thr Tyr Lys Val Leu Ser Leu Val Leu Ser Val
                20                  25                  30

Cys Val Leu Thr Thr Ile Leu Gly Cys Ile Phe Gly Leu Lys Pro Ser
            35                  40                  45

Cys Ala Lys Glu Val Lys Ser Cys Lys Gly Arg Cys Phe Glu Arg Thr
        50                  55                  60

Phe Gly Asn Cys Arg Cys Asp Ala Ala Cys Val Glu Leu Gly Asn Cys
65                  70                  75                  80

Cys Leu Asp Tyr Gln Glu Thr Cys Ile Glu Pro Glu His Ile Trp Thr
                85                  90                  95

Cys Asn Lys Phe Arg Cys Gly Glu Lys Arg Leu Thr Arg Ser Leu Cys
               100                 105                 110

Ala Cys Ser Asp Asp Cys Lys Asp Lys Gly Asp Cys Cys Ile Asn Tyr
           115                 120                 125

Ser Ser Val Cys Gln Gly Glu Lys Ser Trp Val Glu Pro Cys Glu
       130                 135                 140

Ser Ile Asn Glu Pro Gln Cys Pro Ala Gly Phe Glu Thr Pro Pro Thr
145                 150                 155                 160

Leu Leu Phe Ser Leu Asp Gly Phe Arg Ala Glu Tyr Leu His Thr Trp
                165                 170                 175

```
Gly Gly Leu Leu Pro Val Ile Ser Lys Leu Lys Lys Cys Gly Thr Tyr
            180                 185                 190

Thr Lys Asn Met Arg Pro Val Tyr Pro Thr Lys Thr Phe Pro Asn His
        195                 200                 205

Tyr Ser Ile Val Thr Gly Leu Tyr Pro Glu Ser His Gly Ile Ile Asp
    210                 215                 220

Asn Lys Met Tyr Asp Pro Lys Met Asn Ala Ser Phe Ser Leu Lys Ser
225                 230                 235                 240

Lys Glu Lys Phe Asn Pro Glu Trp Tyr Lys Gly Glu Pro Ile Trp Val
                245                 250                 255

Thr Ala Lys Tyr Gln Gly Leu Lys Ser Gly Thr Phe Phe Trp Pro Gly
            260                 265                 270

Ser Asp Val Glu Ile Asn Gly Ile Phe Pro Asp Ile Tyr Lys Met Tyr
        275                 280                 285

Asn Gly Ser Val Pro Phe Glu Glu Arg Ile Leu Ala Val Leu Gln Trp
    290                 295                 300

Leu Gln Leu Pro Lys Asp Glu Arg Pro His Phe Tyr Thr Leu Tyr Leu
305                 310                 315                 320

Glu Glu Pro Asp Ser Ser Gly His Ser Tyr Gly Pro Val Ser Ser Glu
                325                 330                 335

Val Ile Lys Ala Leu Gln Arg Val Asp Gly Met Val Gly Met Leu Met
            340                 345                 350

Asp Gly Leu Lys Glu Leu Asn Leu His Arg Cys Leu Asn Leu Ile Leu
        355                 360                 365

Ile Ser Asp His Gly Met Glu Gln Gly Ser Cys Lys Lys Tyr Ile Tyr
    370                 375                 380

Leu Asn Lys Tyr Leu Gly Asp Val Lys Asn Ile Lys Val Ile Tyr Gly
385                 390                 395                 400

Pro Ala Ala Arg Leu Arg Pro Ser Asp Val Pro Asp Lys Tyr Tyr Ser
                405                 410                 415

Phe Asn Tyr Glu Gly Ile Ala Arg Asn Leu Ser Cys Arg Glu Pro Asn
            420                 425                 430

Gln His Phe Lys Pro Tyr Leu Lys His Phe Leu Pro Lys Arg Leu His
        435                 440                 445

Phe Ala Lys Ser Asp Arg Ile Glu Pro Leu Thr Phe Tyr Leu Asp Pro
    450                 455                 460

Gln Trp Gln Leu Ala Leu Asn Pro Ser Glu Arg Lys Tyr Cys Gly Ser
465                 470                 475                 480

Gly Phe His Gly Ser Asp Asn Val Phe Ser Asn Met Gln Ala Leu Phe
                485                 490                 495

Val Gly Tyr Gly Pro Gly Phe Lys His Gly Ile Glu Ala Asp Thr Phe
            500                 505                 510

Glu Asn Ile Glu Val Tyr Asn Leu Met Cys Asp Leu Leu Asn Leu Thr
        515                 520                 525

Pro Ala Pro Asn Asn Gly Thr His Gly Ser Leu Asn His Leu Leu Lys
    530                 535                 540

Asn Pro Val Tyr Thr Pro Lys His Pro Lys Glu Val His Pro Leu Val
545                 550                 555                 560

Gln Cys Pro Phe Thr Arg Asn Pro Arg Asp Asn Leu Gly Cys Ser Cys
                565                 570                 575

Asn Pro Ser Ile Leu Pro Ile Glu Asp Phe Gln Thr Gln Phe Asn Leu
            580                 585                 590

Thr Val Ala Glu Glu Lys Ile Ile Lys His Glu Thr Leu Pro Tyr Gly
```

```
                        595                 600                 605
Arg Pro Arg Val Leu Gln Lys Glu Asn Thr Ile Cys Leu Leu Ser Gln
610                 615                 620

His Gln Phe Met Ser Gly Tyr Ser Gln Asp Ile Leu Met Pro Leu Trp
625                 630                 635                 640

Thr Ser Tyr Thr Val Asp Arg Asn Asp Ser Phe Ser Thr Glu Asp Phe
                645                 650                 655

Ser Asn Cys Leu Tyr Gln Asp Phe Arg Ile Pro Leu Ser Pro Val His
            660                 665                 670

Lys Cys Ser Phe Tyr Lys Asn Asn Thr Lys Val Ser Tyr Gly Phe Leu
        675                 680                 685

Ser Pro Pro Gln Leu Asn Lys Asn Ser Ser Gly Ile Tyr Ser Glu Ala
    690                 695                 700

Leu Leu Thr Thr Asn Ile Val Pro Met Tyr Gln Ser Phe Gln Val Ile
705                 710                 715                 720

Trp Arg Tyr Phe His Asp Thr Leu Leu Arg Lys Tyr Ala Glu Glu Arg
                725                 730                 735

Asn Gly Val Asn Val Val Ser Gly Pro Val Phe Asp Phe Asp Tyr Asp
            740                 745                 750

Gly Arg Cys Asp Ser Leu Glu Asn Leu Arg Gln Lys Arg Arg Val Ile
        755                 760                 765

Arg Asn Gln Glu Ile Leu Ile Pro Thr His Phe Phe Ile Val Leu Thr
    770                 775                 780

Ser Cys Lys Asp Thr Ser Gln Thr Pro Leu His Cys Glu Asn Leu Asp
785                 790                 795                 800

Thr Leu Ala Phe Ile Leu Pro His Arg Thr Asp Asn Ser Glu Ser Cys
                805                 810                 815

Val His Gly Lys His Asp Ser Ser Trp Val Glu Glu Leu Leu Met Leu
            820                 825                 830

His Arg Ala Arg Ile Thr Asp Val Glu His Ile Thr Gly Leu Ser Phe
        835                 840                 845

Tyr Gln Gln Arg Lys Glu Pro Val Ser Asp Ile Leu Lys Leu Lys Thr
    850                 855                 860

His Leu Pro Thr Phe Ser Gln Glu Asp
865                 870

<210> SEQ ID NO 15
<211> LENGTH: 1173
<212> TYPE: DNA
<213> ORGANISM: Homo sapiens
<220> FEATURE:
<223> OTHER INFORMATION: 3'UTR domain of the ENPP1 gene

<400> SEQUENCE: 15
tgatatgttt tttatcccca aacaccatga atcttttga gagaaccttta tattttatat     60 agtcctctag ctacactatt gcattgttca gaaactgtcg accagagtta gaacggagcc    120
ctcggtgatg cggacatctc agggaaactt gcgtactcag cacagcagtg gagagtgttc    180
ctgttgaatc ttgcacatat ttgaatgtgt aagcattgta tacattgatc aagttcgggg    240
gaataaagac agaccacacc taaaactgcc tttctgcttc tcttaaagga gaagtagctg    300
tgaacattgt ctggatacca gatatttgaa tctttcttac tattggtaat aaaccttgat    360
ggcattgggc aaacagtaga cttatagtag ggttggggta gcccatgtta tgtgactatc    420
tttatgagaa ttttaaagtg gttctggata tcttttaact tggagtttca tttcttttca    480
ttgtaatcaa aaaaaaaatt aacagaagcc aaaatacttc tgagaccttg tttcaatctt    540
```

```
tgctgtatat cccctcaaaa tccaagttat taatcttatg tgttttcttt ttaattttt      600 gattggattt ctttagattt aatggttcaa atgagttcaa ctttgaggga cgatctttga     660
atatacttac ctattataaa atcttacttt gtatttgtat ttaaaaaaga aaaatattcc     720
tatcctgctc actggtaatt aacataggtt taaaatggct tcaaatgtgg ccctatagac     780
ggttaaaatt gtaccttatc ttggcaaaac ttcagagcac cagtcagtgc atgcaaggtg     840 ccattttta ttgagatgct tagaatgttt ctttctgtgc acaagactta ccctaccagc      900
agcagagcca ttctctgttg agtggttcat tttgaagttc cacagattga agagaacatg     960
ccaccaatca cctcacatct tcttggtgga catgataaat gacacaatga acttgatttc    1020
tttactacct tgactgtagc tttttatccc tacctgtgaa ccttcaaaga ctgcattaac    1080
ttttaggcta cataggtcaa ttgaggtata atatcagtac accaaagatt tttatatgtc   1140
cttcgtgtga ccattcttca acggcctaag ggc                                1173
```